(12) United States Patent
Nakada et al.

(10) Patent No.: US 8,614,099 B2
(45) Date of Patent: Dec. 24, 2013

(54) FRET DETECTION METHOD AND DEVICE

(75) Inventors: Shigeyuki Nakada, Tamano (JP);
Noriaki Kimura, Tamano (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 947 days.

(21) Appl. No.: 12/675,323

(22) PCT Filed: Aug. 30, 2007

(86) PCT No.: PCT/JP2007/066849
§ 371 (c)(1),
(2), (4) Date: Feb. 25, 2010

(87) PCT Pub. No.: WO2009/028062
PCT Pub. Date: Mar. 5, 2009

(65) Prior Publication Data
US 2010/0312482 A1    Dec. 9, 2010

(51) Int. Cl.
*G01N 21/76* (2006.01)
*G01N 21/64* (2006.01)

(52) U.S. Cl.
USPC ........ 436/172; 436/164; 436/166; 422/82.05; 422/82.08

(58) Field of Classification Search
None
See application file for complete search history.

(56) References Cited

U.S. PATENT DOCUMENTS

| 5,776,782 | A | 7/1998 | Tsuji |
|---|---|---|---|
| 6,886,977 | B2 | 5/2005 | Kaminski et al. |
| 2006/0287337 | A1 | 12/2006 | Reiss et al. |

FOREIGN PATENT DOCUMENTS

| EP | 1145004 B1 | 4/2004 |
|---|---|---|
| JP | 07-229835 A | 8/1995 |
| JP | 10-227739 A | 8/1998 |
| JP | 10-332594 A | 12/1998 |
| JP | 2002-535655 A | 10/2002 |
| JP | 2005-037399 A | 2/2005 |
| JP | 2005-519636 A | 7/2005 |
| JP | 2005-207823 A | 8/2005 |
| JP | 2006-054347 A | 2/2006 |

OTHER PUBLICATIONS

"Autofluorescence MIT Flow Cytometry Core Facility", http://web.mit.edu/flowcytometry/www/autofluorescenceonly.pdf, no date.*
"Fluorescence Resonance Energy Transfer (FRET) Microscopy", Microscopy Resource Center, 2012.*
Berney and Danuser. "FRET or No FRET: A Quantitative Comparison", Biophys. J., 2003, v. 84, pp. 3992-4010.*
Shigeyuki Nakada et al., Development of Fluorescence Lifetime FRET Flow Cytometer, Mitsui Engineering & Shipbuilding Co., Ltd., GIHO, Mar. 31, 2007, pp. 54-71, No. 190, Mitsui Engineering & Shipbuilding GIHO Editorials, Tokyo, Japan.

* cited by examiner

*Primary Examiner* — Yelena G Gakh
(74) *Attorney, Agent, or Firm* — Global IP Counselors, LLP

(57) ABSTRACT

When FRET efficiency is measured quantitatively by removing uncertain elements of fluorescence detection information, calibration information prestored in a storage means while including at least the leak rate of donor fluorescence component emitted from a donor molecule, the leak rate of acceptor fluorescence component emitted from an acceptor molecule, and the non-FRET fluorescence lifetime of the donor fluorescence component when FRET is not generated out of the fluorescence of a measurement object sample is acquired. The FRET fluorescence lifetime of the donor fluorescence component is then determined using the intensity information and phase information of fluorescence of the measurement object sample, the leak rate of donor fluorescence component and the leak rate of acceptor fluorescence component, thus determining the FRET fluorescence efficiency.

22 Claims, 17 Drawing Sheets

FRET DETECTION METHOD AND DEVICE

TECHNICAL FIELD

The present invention relates to a method of and a device for detecting FRET (Fluorescence Resonance Energy Transfer), in which the energy of a donor molecule transfers to the energy of an acceptor molecule. More specifically, the present invention relates to a FRET detection technology for detecting interaction between a pair of a donor molecule (fluorescent molecule) and an acceptor molecule (fluorescent molecule) using fluorescence.

BACKGROUND ART

Analysis of protein functions has recently become important as post-genome related technology in the medical, pharmaceutical, and food industries. Particularly, in order to analyze actions of cells, it is necessary to research interactions (binding and separation) between a type of protein and another type of protein (or a low molecule compound) which are living substances in a living cell.

The interactions between a type of protein and another type of protein (or a low molecule compound) have been recently analyzed using a fluorescence resonance energy transfer (FRET) phenomenon. Interactions between molecules are herein detected within a range of several nanometers using fluorescence. Such interaction detection using the FRET phenomenon is mainly performed with a microscope system.

For example, Japanese Laid-Open Patent Application No. 2005-207823 discloses a single molecule fluorescence analysis using FRET. Japanese Laid-Open Patent Application No. 2005-207823 proposes a fluorescence spectral analysis method in which a fluorescence correlation analysis method or a fluorescence-intensity distribution analysis is performed based on received fluorescence using the FRET phenomenon.

DISCLOSURE OF THE INVENTION

In this method, however, the number of samples (e.g., cells) is limited to at most about several dozen to detect FRET in a short period of time. In other words, it is difficult to statistically analyze a large number of cells as analysis targets in a short period of time. Further, in conventional methods, only fluorescence intensity is measured. However, fluorescence intensity depends on the amount of fluorescent protein label attached to a cell, which makes it impossible to completely eliminate the uncertainties of measured fluorescence information. For this reason, such conventional methods have a problem that it is difficult to quantitatively detect the degree of occurrence of FRET.

In order to solve the above problem, it is an object of the present invention to provide a method of and a device for detecting FRET capable of quantitatively measuring the degree of occurrence of FRET (e.g., FRET efficiency) of a sample containing a donor molecule and an acceptor molecule by eliminating the uncertainties of fluorescence detection information resulting from the amount of fluorescent protein label attached and by eliminating the uncertainties of fluorescence detection information resulting from the broadening of wavelength range of fluorescence emitted by the donor molecule and the broadening of wavelength range of fluorescence emitted by the acceptor molecule.

In order to achieve the object, the present invention provides a FRET detection method of detecting FRET (Fluorescence Resonance Energy Transfer) in which energy of a first molecule is transferred to a second molecule.

The method includes the steps of:
A FRET detection method of detecting FRET (Fluorescence Resonance Energy Transfer) in which energy of a donor molecule is transferred to an acceptor molecule, the method comprising the steps of:

a) measuring fluorescence emitted from each of samples by two or more detection sensors having different light-receiving wavelength bands, each of the samples being labeled with a donor molecule and an acceptor molecule and being irradiated with laser light whose intensity is modulated at a predetermined frequency, to acquire detection values including fluorescence intensity information and phase information on the fluorescence emitted from each of the samples;

b) reading calibration information previously stored in a memory means, which includes at least a first intensity ratio that is a ratio between fluorescence intensities at the light-receiving wavelength bands of a donor molecule fluorescence component emitted from the donor molecule included in the fluorescence emitted from each of the samples, phase information on the donor molecule fluorescence component relative to the modulated laser light, a second intensity ratio that is a ratio between fluorescence intensities at the light-receiving wavelength bands of an acceptor molecule fluorescence component emitted from the acceptor molecule included in the fluorescence, phase information on the acceptor molecule fluorescence component relative to the laser light, and a non-FRET fluorescence lifetime of the donor molecule fluorescence component when the FRET does not occur, which is a lifetime defined by assuming that fluorescence emitted from the donor molecule excited by laser light is a relaxation response of a first-order lag system;

c) calculating fluorescence intensity information and phase information on the fluorescence at each of the light-receiving wavelength bands, based on the detection values, and determining a FRET fluorescence lifetime of the donor molecule fluorescence component, which is defined by assuming that fluorescence emitted from the donor molecule excited by laser light is a relaxation response of a first-order lag system, using the calculated fluorescence intensity information, the calculated phase information, the first intensity ratio, the phase information on the donor molecule fluorescence component, the second intensity ratio, the phase information on the acceptor molecule fluorescence component; and d) determining information on FRET occurrence using a ratio between the FRET fluorescence lifetime of the donor molecule fluorescence component and the non-FRET fluorescence lifetime of the donor molecule fluorescence component.

In the step d), FRET efficiency $E_t$ is preferably determined as the information on the occurrence of FRET, which is represented by $1-(\tau_d^*/\tau_d)$, wherein $\tau_d$ is the non-FRET fluorescence lifetime of the donor molecule fluorescence component and $\tau_d^*$ is the FRET fluorescence lifetime of the donor molecule fluorescence component.

Preferably, in the step c), fluorescence intensity information and phase information on each of the samples are calculated based on each of the detection values and the FRET fluorescence lifetime is determined based on the calculated multiple pieces of fluorescence intensity information and phase information.

Also preferably, in the step c), the fluorescence intensity information and the phase information calculated at each of the light-receiving wavelength bands are represented as a vector, and fluorescence intensity information and phase information on the donor molecule fluorescence component and fluorescence intensity information and phase information on a FRET component of an acceptor molecule fluorescence component which is emitted by the donor molecule on the occurrence of FRET are calculated at, and the FRET fluorescence lifetime is determined by using the calculated information.

And also preferably, the light-receiving wavelength bands include a first wavelength band centered around a peak wavelength at which a fluorescence intensity of the donor molecule fluorescence component is maximum and a second wavelength band centered around a peak wavelength at which a fluorescence intensity of the acceptor molecule fluorescence component is maximum. In the step c), fluorescence intensity information and phase information on the donor molecule fluorescence component emitted are calculated using at least the second intensity ratio and the vector at the first wavelength band represented by the detection values acquired from the detection sensors with the first wavelength band, and fluorescence intensity information and phase information on the FRET component are calculated using at least the first intensity ratio and the vector at the second wavelength band represented by the detection values acquired from the detection sensors with the second wavelength band.

Preferably, the memory means previously stores fluorescence intensity information and phase information on a directly-excited fluorescence component of the acceptor molecule fluorescence component, the directly-excited fluorescence component being emitted by the acceptor molecule directly excited by the laser light, in the step b), fluorescence intensity information and phase information on the directly-excited fluorescence component are read from the memory means to represent the information on the directly-excited fluorescence component as a vector, and in the step c), fluorescence intensity information and phase information on the acceptor molecule fluorescence component emitted at the time when the FRET occurs are calculated using at least the vector of the directly-excited fluorescence component and the vector at the second wavelength band.

Also preferably, the memory means previously stores fluorescence intensity information and phase information on a directly-excited fluorescence component of the acceptor molecule fluorescence component, the directly-excited fluorescence component being emitted by the acceptor molecule directly excited by the laser light, in the step b), fluorescence intensity information and phase information on the directly-excited fluorescence component are read from the memory means and then represented as a vector of the directly-excited fluorescence component, and in the step c), phase information on the FRET component is further calculated using at least the vector at the second wavelength band and the first intensity ratio, and a FRET fluorescence lifetime of the acceptor molecule fluorescence component emitted at the time when the FRET occurs and a non-FRET fluorescence lifetime of the acceptor molecule fluorescence component emitted at the time when the FRET does not occur are determined using the calculated phase information on the FRET component and the vector of the directly-excited fluorescence component, and a FRET fluorescence lifetime of the donor molecule fluorescence component is determined using the FRET fluorescence lifetime of the acceptor molecule fluorescence component and the non-FRET fluorescence lifetime of the acceptor molecule fluorescence component.

Preferably, the method further includes the steps of:

preparing a predetermined sample which is each of the samples unlabeled with the donor molecule and the acceptor molecule and emits autofluorescence when irradiated with the laser light;

measuring, at each of the light-receiving wavelength bands, the autofluorescence emitted by the predetermined sample which is irradiated with the laser light;

calculating fluorescence intensity information and phase information on the autofluorescence from the measured autofluorescence within each of the light-receiving wavelength bands to store the calculated fluorescence intensity information and phase information in the memory means;

wherein in the step b), the stored fluorescence intensity information and the phase information on the autofluorescence are read from the memory means and the read fluorescence intensity information and the phase information on the autofluorescence are represented as a vector, and in the step c), the vector of the autofluorescence is subtracted from each vector at the light-receiving wavelength bands of the samples to be measured, and the FRET fluorescence lifetime is determined using a vector obtained by the subtraction.

Also preferably, the autofluorescence is measured by each of the detection sensors by irradiating the predetermined sample as a measuring object with laser light whose intensity is modulated at a predetermined frequency.

Still also preferably, the method further includes the steps of:

preparing a non-FRET sample which is labeled with the donor molecule and the acceptor molecule and which has been treated not to cause FRET;

measuring, at each of the light-receiving wavelength bands, fluorescence emitted by the non-FRET sample which is irradiated with the laser light; and calculating fluorescence intensity information and phase information on the a directly-excited fluorescence component emitted by the acceptor molecule directly excited by laser light within each of the light-receiving wavelength bands from the measured fluorescence, using the first intensity ratio previously stored in the memory means, the phase information on the donor molecule fluorescence component, the second intensity ratio previously stored in the memory means, and the phase information on the acceptor molecule fluorescence component, to store the calculated fluorescence intensity information and phase information in the memory means.

Still preferably, the non-FRET sample is a sample obtained by labeling, with the donor molecule and the acceptor molecule, a predetermined sample which emits autofluorescence when excited by the laser light.

The method further includes the steps of:

preparing the predetermined sample;

measuring, at each of the light-receiving wavelength bands, the autofluorescence emitted by the predetermined sample which is irradiated with the laser light;

calculating fluorescence intensity information and phase information on the autofluorescence from the measured autofluorescence within each of the light-receiving wavelength bands, to store the calculated fluorescence intensity information and phase information on the autofluorescence in the memory means;

subtracting an autofluorescence vector representing the fluorescence intensity information and phase information on the autofluorescence from a non-FRET sample vector representing fluorescence intensity information and phase information on fluorescence emitted by the non-FRET sample; and calculating a directly-excited fluorescence component vector representing the fluorescence intensity information and phase information on the directly-excited fluorescence component, using a vector obtained by the subtraction.

Preferably, the method further comprising the steps of:

preparing a donor molecule sample which is labeled with only the donor molecule;

measuring, at each of the light-receiving wavelength bands, fluorescence emitted by the donor molecule of the donor molecule sample which is irradiated with the laser light;

calculating fluorescence intensity information and phase information on the measured fluorescence emitted by the donor molecule sample within each of the light-receiving wavelength bands, to obtain the first intensity ratio; and storing the phase information on the measured fluorescence and the first intensity ratio.

More preferably, the donor molecule sample is a sample obtained by labeling, with the donor molecule, a predetermined sample which emits autofluorescence when excited by the laser light, the method further comprising the steps of:

preparing the predetermined sample;

measuring, at each of the light-receiving wavelength bands, the autofluorescence emitted by the predetermined sample which is irradiated with the laser light;

calculating fluorescence intensity information and phase information on the autofluorescence from the measured autofluorescence within each of the light-receiving wavelength bands to store the calculated fluorescence intensity information and phase information in the memory means;

subtracting an autofluorescence vector representing the fluorescence intensity information and phase information on the autofluorescence from a donor molecule sample vector representing fluorescence intensity information and phase information on fluorescence emitted by the donor molecule sample; and calculating the fluorescence intensity information and phase information on the fluorescence emitted by the donor molecule sample, using a vector obtained by the subtraction.

And also preferably, the method further includes the steps of:

preparing an acceptor molecule sample which is labeled with only the acceptor molecule;

measuring, at each of the light-receiving wavelength bands, fluorescence emitted by the acceptor molecule of the acceptor molecule sample which is irradiated with the laser light;

calculating fluorescence intensity information and phase information on the measured fluorescence emitted by the acceptor molecule sample within each of the light-receiving wavelength bands, to obtain the second intensity ratio; and storing the phase information on the measured fluorescence and the second intensity ratio.

More preferably, the acceptor molecule sample is a sample obtained by labeling, with the acceptor molecule, a predetermined sample which emits autofluorescence when excited by the laser light.

The method further includes the steps of:

preparing the predetermined sample;

measuring, at each of the light-receiving wavelength bands, the autofluorescence emitted by the predetermined sample which is irradiated with the laser light;

calculating fluorescence intensity information and phase information on the autofluorescence from the measured autofluorescence within each of the light-receiving wavelength bands, to store the calculated fluorescence intensity information and phase information in the memory means;

subtracting an autofluorescence vector representing the fluorescence intensity information and phase information on the autofluorescence from an acceptor molecule sample vector representing fluorescence intensity information and phase information on fluorescence emitted by the acceptor molecule sample; and calculating the fluorescence intensity information and phase information on the fluorescence emitted by the acceptor molecule sample, using a vector obtained by the subtraction.

The present invention also provides a device for detecting FRET (Fluorescence Resonance Energy Transfer), in which energy of a first molecule transfers to a second molecule. The device includes:

an information acquiring unit which acquires detection values, each values including fluorescence intensity information and phase information on fluorescence emitted by each of the samples to be measured by allowing two or more detection sensors different in light-receiving wavelength band to receive fluorescence emitted by each of the samples to be measured, each of the samples being labeled with a donor molecule and an acceptor molecule and being irradiated with laser light whose intensity is modulated at a predetermined frequency;

a memory means for previously storing calibration information including at least a first intensity ratio that is a ratio between fluorescence intensities at the light-receiving wavelength bands of a donor molecule fluorescence component emitted by the donor molecule included in the fluorescence emitted by each of the samples to be measured, phase information on the donor molecule fluorescence component, an acceptor intensity ratio that is a ratio between fluorescence intensities at the light-receiving wavelength bands of an acceptor molecule fluorescence component emitted by the acceptor molecule, phase information of the acceptor molecule fluorescence component, and a non-FRET fluorescence lifetime, of the donor molecule fluorescence component emitted at the time when the FRET does not occur, which is a lifetime defined by assuming that fluorescence emitted by the donor molecule excited by laser light is a relaxation response of a first-order lag system;

a FRET fluorescence lifetime calculating unit which calculates fluorescence intensity information and phase information on fluorescence within each of the light-receiving wavelength bands emitted by each of the samples to be measured based on the detection values acquired by the detected information acquiring unit, and determines a FRET fluorescence lifetime of the donor molecule fluorescence component, which is defined by assuming that fluorescence emitted by the donor molecule excited by laser light is a relaxation response of a first-order lag system, by using the calculated fluorescence intensity information, the calculated phase information, the first intensity ratio read from the memory means, the phase information on the donor molecule fluorescence component, the second intensity ratio, and the phase information on the acceptor molecule fluorescence component; and a FRET occurrence information calculating unit which determines information on the occurrence of FRET represented by a ratio between the FRET fluorescence lifetime of the donor molecule fluorescence component and the non-FRET fluorescence lifetime of the donor molecule fluorescence component.

Preferably, in the FRET fluorescence lifetime calculating unit, the fluorescence intensity information and the phase information calculated from each of the detection values are represented as a vector, and fluorescence intensity information and phase information on the donor molecule fluorescence component and fluorescence intensity information and phase information on a FRET component of an acceptor molecule fluorescence component which is emitted by the acceptor molecule at the time when the FRET occurs, are calculated using the vector, the first intensity ratio, the phase information on the donor molecule fluorescence component, the second intensity ratio of the acceptor molecule fluorescence component, and the phase information on the acceptor molecule fluorescence component, and the FRET fluorescence lifetime is determined by using the calculated information.

Also preferably, the respective light-receiving wavelength bands of the sensors are a first wavelength band centered around a peak wavelength at which a fluorescence intensity of the donor molecule fluorescence component is maximum and a second wavelength band centered around a peak wavelength at which a fluorescence intensity of the acceptor molecule fluorescence component is maximum, and the FRET fluorescence lifetime calculating unit calculates fluorescence intensity information and phase information on the donor molecule fluorescence component by using at least a vector at the first wavelength band determined from the detection value acquired from one of the detection sensors with the first wavelength band and the second intensity ratio, and calculates fluorescence intensity information and phase information on the FRET component by using at least a vector at the second wavelength band represented by the detection value acquired from one of the detection sensors with the second wavelength band and the first intensity ratio.

Preferably, the device further includes an autofluorescence calibration unit. The autofluorescence calibration unit acquires a detection value including fluorescence intensity information and phase information at each of the light-receiving wavelength bands from each of the detection sensors by irradiating, with the laser, light a predetermined sample which is each of the samples unlabeled with the donor molecule and the acceptor molecule and emits autofluorescence when irradiated with the laser light, calculates fluorescence intensity information and phase information on the autofluorescence within each of the light-receiving wavelength bands, and stores the calculated fluorescence intensity information and the calculated phase information on the autofluorescence in the memory means, and in the FRET fluorescence lifetime calculating unit, a vector representing the fluorescence intensity information and the phase information on the autofluorescence is subtracted from a vector representing information on fluorescence within each of the light-receiving wavelength bands emitted by the sample to be measured, and the FRET fluorescence lifetime is determined using a vector obtained by the subtraction.

Preferably, the device further includes a non-FRET calibration unit. The non-FRET calibration unit calculates fluorescence intensity information and phase information on fluorescence within each of the light-receiving wavelength bands emitted by a non-FRET sample, which has the donor and acceptor molecules attached thereto and which has been treated so as not to cause FRET, when a detection value including fluorescence intensity information and phase information, at each of the light-receiving wavelength bands is acquired from each of the detection sensors by irradiating the non-FRET sample with the laser light, and calculates fluorescence intensity information and phase information on a directly-excited fluorescence component emitted by the acceptor molecule directly excited by the laser light by using the calculated fluorescence intensity information, the calculated phase information, the first intensity ratio, the phase information on the donor molecule fluorescence component, the second intensity ratio, and the phase information on the acceptor molecule fluorescence component, and derives a directly-excited fluorescence component vector representing the calculated information, and stores a derived result in the memory means, and the FRET fluorescence lifetime calculating unit determines the FRET fluorescence lifetime by using the directly-excited fluorescence component vector.

Preferably, the device further includes a donor molecule calibration unit. The donor molecule calibration unit calculates fluorescence intensity information and phase information on fluorescence within each of the light-receiving wavelength bands emitted by a donor molecule sample, which is each of the samples labeled with only the donor molecule, when the donor molecule sample irradiated with the laser light emits fluorescence and a detection value including fluorescence intensity information and phase information on the fluorescence within each of the light-receiving wavelength bands emitted by the donor molecule sample is acquired from each of the detection sensors, and calculates the first intensity ratio, and stores the calculated first intensity ratio and the calculated phase information on fluorescence emitted by the donor molecule sample in the memory means.

Preferably, the device further includes an acceptor molecule calibration unit. The acceptor molecule calibration unit calculates fluorescence intensity information and phase information on fluorescence within each of the light-receiving wavelength bands emitted by an acceptor molecule sample, which is each of the samples labeled with only the acceptor molecule, when the acceptor molecule sample irradiated with the laser light emits fluorescence and a detection value including fluorescence intensity information and phase information on the fluorescence within each of the light-receiving wavelength bands emitted by the acceptor molecule sample is acquired from each of the detection sensors, and calculates, the second intensity ratio, and stores the calculated second intensity ratio and the calculated phase information on fluorescence emitted by the acceptor molecule sample in the memory means.

EFFECTS OF THE INVENTION

According to the present invention, it is possible to provide a method of and a device for detecting FRET capable of quantitatively measuring the degree of occurrence of FRET (e.g., FRET efficiency) of a sample to be measured, which is obtained by, for example, attaching a donor molecule (fluorescent protein) and an acceptor molecule (fluorescent protein) to a cell, by eliminating the uncertainties of fluorescence detection information resulting from the amount of fluorescent protein label attached and by eliminating the uncertainties of fluorescence detection information resulting from the overlap between the light-receiving wavelength bands of fluorescence emitted by the donor molecule and the wavelength band of fluorescence emitted by the acceptor molecule.

BEST MODE FOR CARRYING OUT THE INVENTION

Hereinbelow, a method of and a device for detecting FRET according to the present invention will be described in detail based on a flow cytometer.

Figure 1:
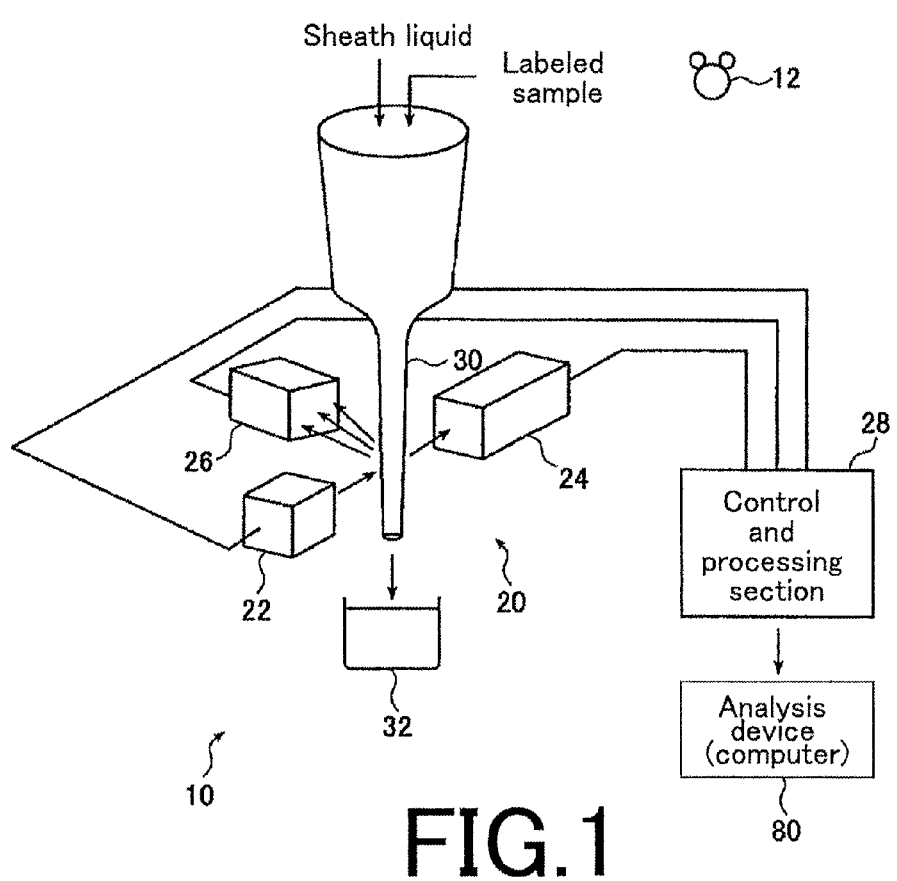
FIG. 1 is a schematic configuration diagram of a flow cytometer using a FRET detection device according to the present invention.

FIG. 1 is a schematic configuration diagram of a flow cytometer 10 using a FRET detection device according to the present invention.

The flow cytometer 10 mainly includes a signal processing device 20 and an analysis device (computer) 80.

The signal processing device 20 irradiates a FRET detection target sample 12 (hereinafter, referred to as a "FRET sample 12") with laser light and detects and processes a fluorescence signal of fluorescence emitted by the FRET sample 12. The FRET sample 12 is obtained by labeling a receptor sample such as a specific cell (hereinafter, referred to as a "cell") with a donor molecule and an acceptor molecule by chemical or physical bonding. The analysis device 80 analyzes the FRET sample 12 based on a processing result obtained from the signal processing device 20. The sample emits autofluorescence when irradiated with laser light. Such autofluorescence becomes a measurement noise component. Therefore, in fact, it is preferred that no autofluorescence be generated. However, a certain degree of autofluorescence is generated, for example, in a case where a cell or the like is irradiated with laser light.

The flow cytometer 10 is one embodiment of the present invention. The flow cytometer 10 is a device in which a plurality of FRET samples suspended in a measurement solution are irradiated with laser light, and the respective fluorescence lifetimes (fluorescence relaxation time constants) of fluorescence components (a fluorescence component within a donor wavelength band and a fluorescence component within an acceptor wavelength band, which will be described later) of fluorescence emitted by each of the FRET samples are calculated to determine FRET efficiency indicating the degree of occurrence of FRET of the FRET sample.

The signal processing device 20 includes a laser light source unit 22, light-receiving units 24 and 26, a control and processing section 28, and a tube line 30. The control and processing section 28 includes a control unit and a processing unit. The control unit modulates the intensity of laser light to be emitted from the laser light source unit 22 at a predetermined frequency. The processing unit processes a fluorescence signal from the FRET sample 12 that flows through the tube line 30 with a sheath liquid that forms a high-speed flow, thereby forming a flow cell.

A recovery container 32 is disposed at the outlet of the tube line 30. The flow cytometer 10 may include a cell sorter for separating a living substance (e.g., specific cells) contained in the FRET samples 12 within a short period of time by irradiation with laser light to recover the living substance in a different recovery container.

The laser light source unit 22 is a light source that emits laser light to excite the donor molecule. For example, in a case where CFP (Cyan Fluorescent Protein) is used as the donor molecule and YFP (Yellow Fluorescent Protein) is used as the acceptor molecule, laser light having a wavelength of 405 to 440 nm is used to mainly excite the donor molecule. More specifically, the laser light source unit 22 is a unit that emits laser light having a wavelength to excite the donor molecule under the condition that its intensity is modulated at a predetermined frequency.

Figure 2:
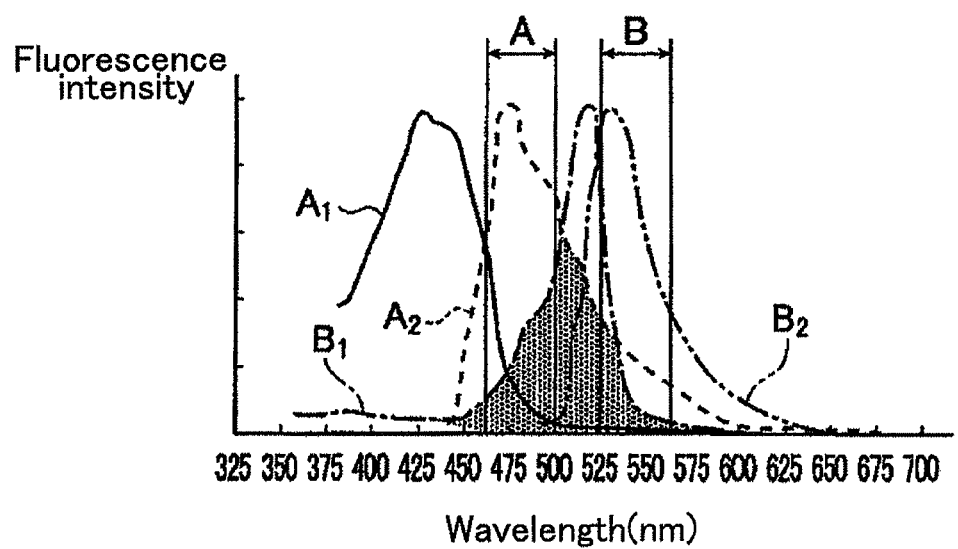
FIG. 2 is a chart showing examples of the energy absorption spectrum and fluorescence spectrum of a donor molecule and examples of the energy absorption spectrum and fluorescence spectrum of an acceptor molecule.
Figure 3:
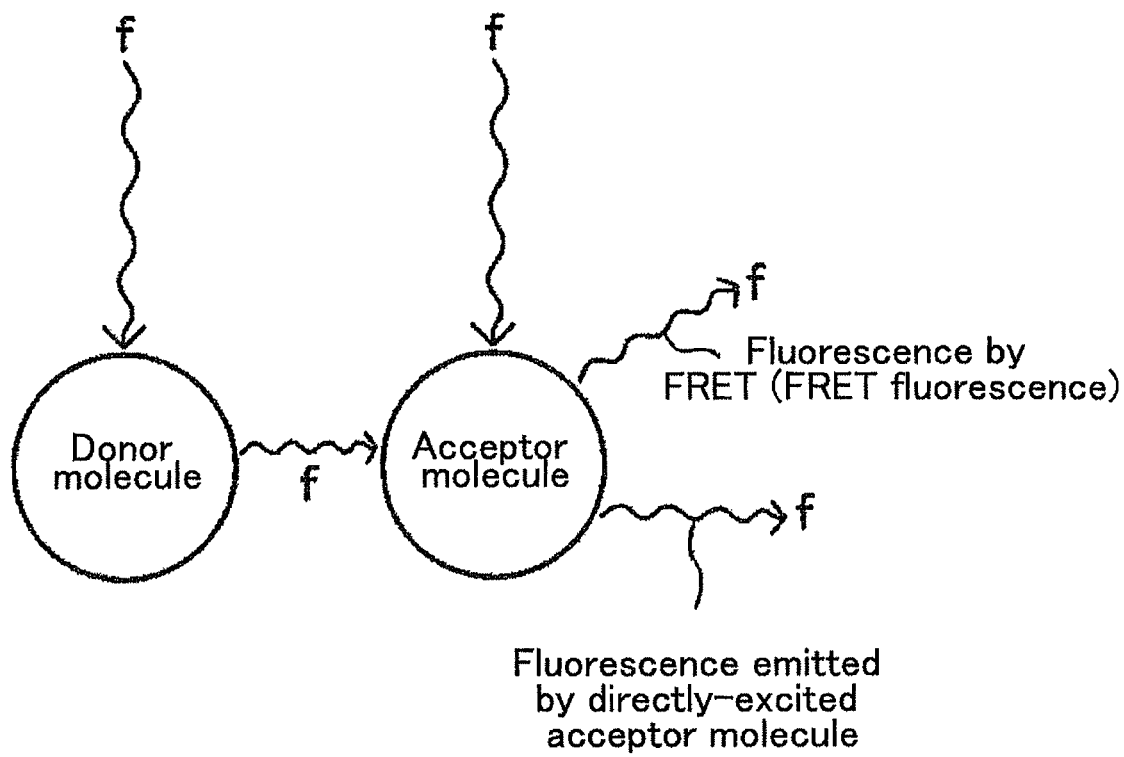
FIG. 3 is a schematic diagram illustrating the occurrence of FRET.

Here, the occurrence of FRET is briefly explained. FIG. 2 is a chart showing examples of the energy absorption spectrum and fluorescence spectrum of the donor molecule and examples of the energy absorption spectrum and fluorescence spectrum of the acceptor molecule. FIG. 3 is a diagram illustrating the occurrence of FRET in an easily understandable manner.

FIG. 2 shows the characteristics of energy absorption and fluorescence emission of the donor and acceptor molecules. In this case, the donor molecule is CFP (Cyan Fluorescent Protein) and the acceptor molecule is YFP (Yellow Fluorescent Protein). In FIG. 2, curve $A_1$ indicates the energy absorption spectrum of CFP, curve $A_2$ indicates the fluorescence emission spectrum of CFP, curve $B_1$ indicates the energy absorption spectrum of YFP, and curve $B_2$ indicates the fluorescence emission spectrum of YFP. In FIG. 2, a hatched area indicates a wavelength band where YFP absorbs the energy of fluorescence emitted by CFP so that FRET occurs.

Generally, FRET occurs by the following mechanism. A donor molecule is excited by laser light, part of the excited donor molecule emits fluorescence, and the energy of the excited donor molecule is partially transferred to an acceptor molecule by the coulomb interaction. Such energy transfer occurs between positions spaced away by a very small distance of 2 nm or less, and indicates interaction (bonding) between molecules. When the energy transfer occurs, the acceptor molecule is excited and emits fluorescence. In order to allow FRET to occur, as shown in FIG. 2, it is necessary for the fluorescence emission wavelength band of the donor molecule and the energy absorption wavelength band of the acceptor molecule to partially overlap each other.

Generally, in a molecule, the peak wavelength of its energy absorption spectrum and the peak wavelength of its fluorescence spectrum are very close to each other unless its fluorescence emission energy is significantly large. As shown in FIG. 2, the same applies to CFP (Cyan Fluorescent Protein) as the donor molecule and to YFP (Yellow Fluorescent Protein) as the acceptor molecule. As described above, in order to allow FRET to occur, it is necessary for the fluorescence emission wavelength band of the donor molecule and the energy absorption wavelength band of the acceptor molecule to partially overlap each other. Therefore, the peak wavelengths of the curves $A_1$, $A_2$, $B_1$, and $B_2$ shown in FIG. 2 are of course concentrated in a narrow wavelength band and these wavelength spectra partially overlap one another. Therefore, in a case where laser light (e.g., laser light modulated at a frequency f) is emitted from the laser light source unit 22 to excite the donor molecule, the acceptor molecule is also directly excited by the laser light so that fluorescence is emitted not only from the donor molecule but also from the acceptor molecule (see FIG. 3).

In the flow cytometer 10, laser light is emitted from the laser light source unit 22, and as a result, the FRET sample 12 to be measured emits autofluorescence (not shown in FIG. 3) emitted by the cell contained therein, fluorescence emitted by the excited donor molecule contained therein, fluorescence emitted by the excited acceptor molecule contained therein, and FRET fluorescence emitted by the acceptor molecule.

The light-receiving unit 24 is disposed so as to be opposite to the laser light source unit 22 with the tube line 30 interposed therebetween. The light-receiving unit 24 is provided with a photoelectric converter. In response to laser light forwardly scattered by the FRET sample 12 passing through a measurement point in the tube line 30, the photoelectric converter outputs a detection signal indicating that the FRET sample 12 is passing through the measurement point. The signal output from the light-receiving unit 24 is supplied to the control and processing section 28, in which the signal is used as a trigger signal indicating the timing of passage of the FRET sample 12 through the measurement point.

On the other hand, the light-receiving unit 26 is disposed so as to be orthogonal to a direction in which laser light is emitted from the laser light source unit 22 and also orthogonal to a direction in which the FRET sample 12 moves in the tube line 30. The light-receiving unit 26 is provided with a photoelectric converter. The photoelectric converter receives fluorescence emitted by the FRET sample 12 irradiated at the measurement point. A photomultiplier and an avalanche photodiode are examples of the photoelectric converter.

Figure 4:
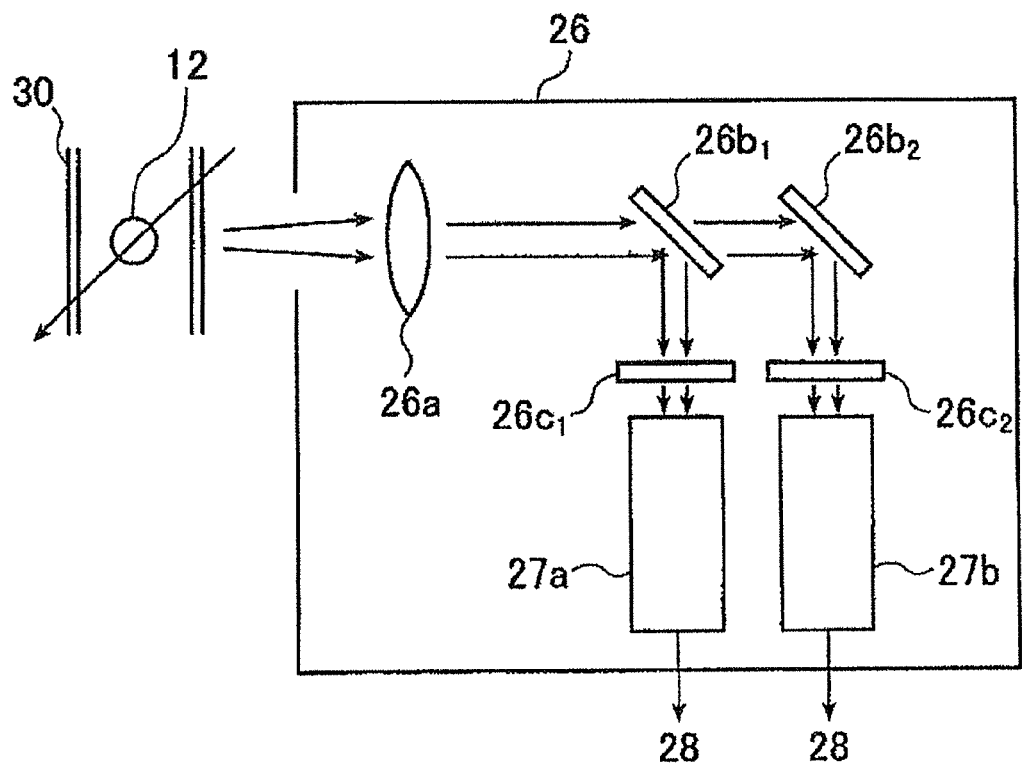
FIG. 4 is a schematic configuration diagram of one example of a light-receiving unit of the flow cytometer shown in FIG. 1.

FIG. 4 is a schematic configuration diagram schematically showing the configuration of one example of the light-receiving unit 26. The light-receiving unit 26 shown in FIG. 4 includes a lens system 26a, dichroic mirrors $26b_1$ and $26b_2$, band-pass filters $26c_1$ and $26c_2$, and photoelectric converters 27a and 27b. The lens system 26a focuses a fluorescence signal of fluorescence emitted by the FRET sample 12. As the photoelectric converters 27a and 27b, photomultipliers, avalanche photodiodes, or the like are used. The lens system 26a is configured to focus fluorescence received by the light-receiving unit 26 on the light-receiving surfaces of the photoelectric converters 27a and 27b.

The dichroic mirrors $26b_1$ and $26b_2$ reflect fluorescence within a predetermined wavelength band but transmits other wavelengths of fluorescence. The reflection wavelength band and transmission wavelength band of the dichroic mirror $26b_1$ are set so that, after filtering by the band-pass filter $26c_1$, fluorescence within a predetermined wavelength band can be introduced into the photoelectric converter 27a. Also, the reflection wavelength band and transmission wavelength band of the dichroic mirror $26b_2$ are set so that, after filtering by the band-pass filter $26c_2$, fluorescence within a predetermined wavelength band can be introduced into the photoelectric converter 27b.

The band-pass filter $26c_1$ is a filter disposed in front of the light-receiving surface of the photoelectric converter 27a and transmits only fluorescence within a predetermined wavelength band. Also, the band-pass filter $26c_2$ is a filter disposed in front of the light-receiving surface of the photoelectric converter 27b and transmits only fluorescence within a predetermined wavelength band. The fluorescence wavelength bands that the filters $26c_1$ and $26c_2$ transmit are set so as to correspond to the wavelength band of fluorescence to be emitted, and are herein different from each other.

In a case where CFP (Cyan Fluorescent Protein) is used as the donor molecule and YFP (Yellow Fluorescent Protein) is used as the acceptor molecule, the fluorescence wavelength bands that the filters $26c_1$ and $26c_2$ transmit are set so that fluorescence emitted by the donor molecule (indicated by the curve $A_2$ in FIG. 2) and fluorescence emitted by the acceptor molecule (indicated by the curve $B_2$ in FIG. 2) can be separately measured. For example, a wavelength band indicated by an arrow A in FIG. 2 is set as a wavelength band (donor wavelength band) that one of the filters transmits so that fluorescence emitted by the donor molecule (donor fluorescence) is mainly transmitted, and a wavelength band indicated by an arrow B in FIG. 2 is set as a wavelength band (acceptor wavelength band) that the other filter transmits so that fluorescence emitted by the acceptor molecule (acceptor fluorescence) is mainly transmitted.

Here, as described above, the wavelength band of the donor fluorescence and the wavelength band of the acceptor fluorescence actually overlap each other, and therefore, transmitted light (fluorescence) within the donor wavelength band contains a leaked acceptor fluorescence component. Also, transmitted light (fluorescence) within the acceptor wavelength band contains a leaked donor fluorescence component. It can be said that such leakage inevitably occurs under conditions where FRET can occur (i.e., under conditions where the fluorescence emission wavelength band of the donor molecule and the energy absorption wavelength band of the acceptor molecule partially overlap each other). In conventional methods for measuring and evaluating the occurrence of FRET, such leaked components are uncertainties that reduce the accuracy of measurement and evaluation. However, the present invention achieves high-accuracy measurement of FRET and high-accuracy evaluation of FRET based on measurement results by taking the influence of such leaked components into consideration.

The photoelectric converters 27a and 27b are each a sensor that converts light received by its photoelectric surface into an electric signal. Each of the photoelectric converters 27a and 27b is provided with a sensor including, for example, a photomultiplier. The light-receiving unit 26 is configured so that the photoelectric converter 27a can receive light within the donor wavelength band and the photoelectric converter 27b can receive light within the acceptor wavelength band.

Figure 5:
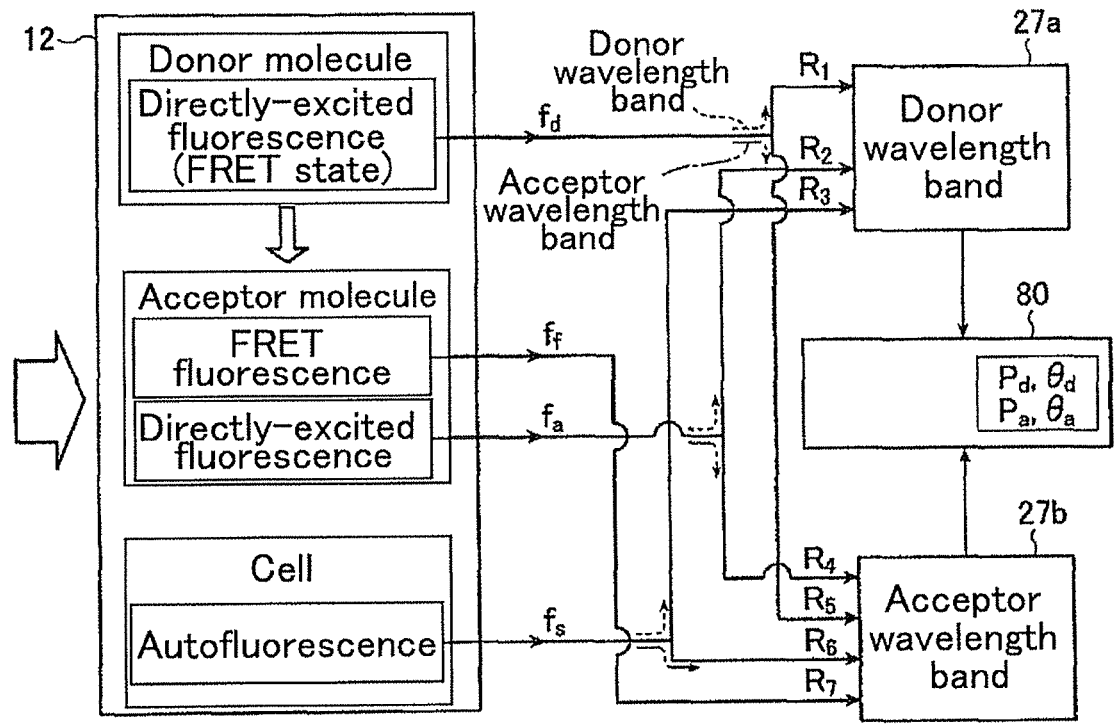
FIG. 5 is a diagram illustrating the components of fluorescence emitted by a FRET sample and the incidence of these fluorescence components into photoelectric converters in the flow cytometer shown in FIG. 1.

FIG. 5 is a schematic diagram illustrating fluorescence components emitted by the FRET sample 12, which is irradiated with laser light emitted from the laser light source unit 22 while flowing through the tube line 30, and the incidence of these fluorescence components into the light-receiving surfaces of the photoelectric converters 27a and 27b. The FRET sample 12 is a sample in which CFP (Cyan Fluorescent Protein) as the donor molecule and YFP (Yellow Fluorescent Protein) as the acceptor molecule are attached to a cell that emits autofluorescence. When laser light is emitted from the laser light source unit 22, the FRET sample 12 that flows through the tube line 30 emits fluorescence $f_d$, fluorescence $f_a$, fluorescence $f_s$, and fluorescence $f_f$. The fluorescence $f_d$ is fluorescence emitted by the donor molecule contained in the FRET sample 12 and directly excited by the laser light. The fluorescence $f_a$ is fluorescence emitted by the acceptor molecule contained in the FRET sample 12 and directly excited by the laser light. The fluorescence $f_s$ is autofluorescence emitted by the cell contained in the FRET sample 12. The fluorescence $f_f$ is FRET fluorescence emitted by the acceptor molecule. Each of the fluorescences is separated by the mirrors and the filters into a donor wavelength band component and an acceptor wavelength band component, and the donor wavelength band components and the acceptor wavelength band components of these fluorescences are introduced into the photoelectric converters 27a and 27b, respectively. Here, the FRET fluorescence $f_f$ is weaker than other fluorescences emitted by direct excitation by laser, and therefore it can be assumed that its donor wavelength band component (leaked component) is sufficiently small.

Light received by the photoelectric converter 27a contains fluorescences indicated by routes $R_1$ to $R_3$ in FIG. 5, and light received by the photoelectric converter 27b contains fluorescences indicated by routes $R_4$ to $R_7$ in FIG. 5. Processing performed by each of the above-mentioned units of the flow cytometer 10 will be described below, which is performed on both the light (fluorescence within the donor wavelength band) received by the photoelectric converter 27a and the light (fluorescence within the acceptor wavelength band) received by the photoelectric converter 27b.

Each of the photoelectric converters 27a and 27b receives light as an optical signal having signal information, and therefore an electric signal output from each of the photoelectric converters 27a and 27b is a fluorescence signal having signal information about phase difference. The fluorescence signal is supplied to the control and processing section 28, and is then amplified by an amplifier and sent to the analysis device 80.

Figure 6:
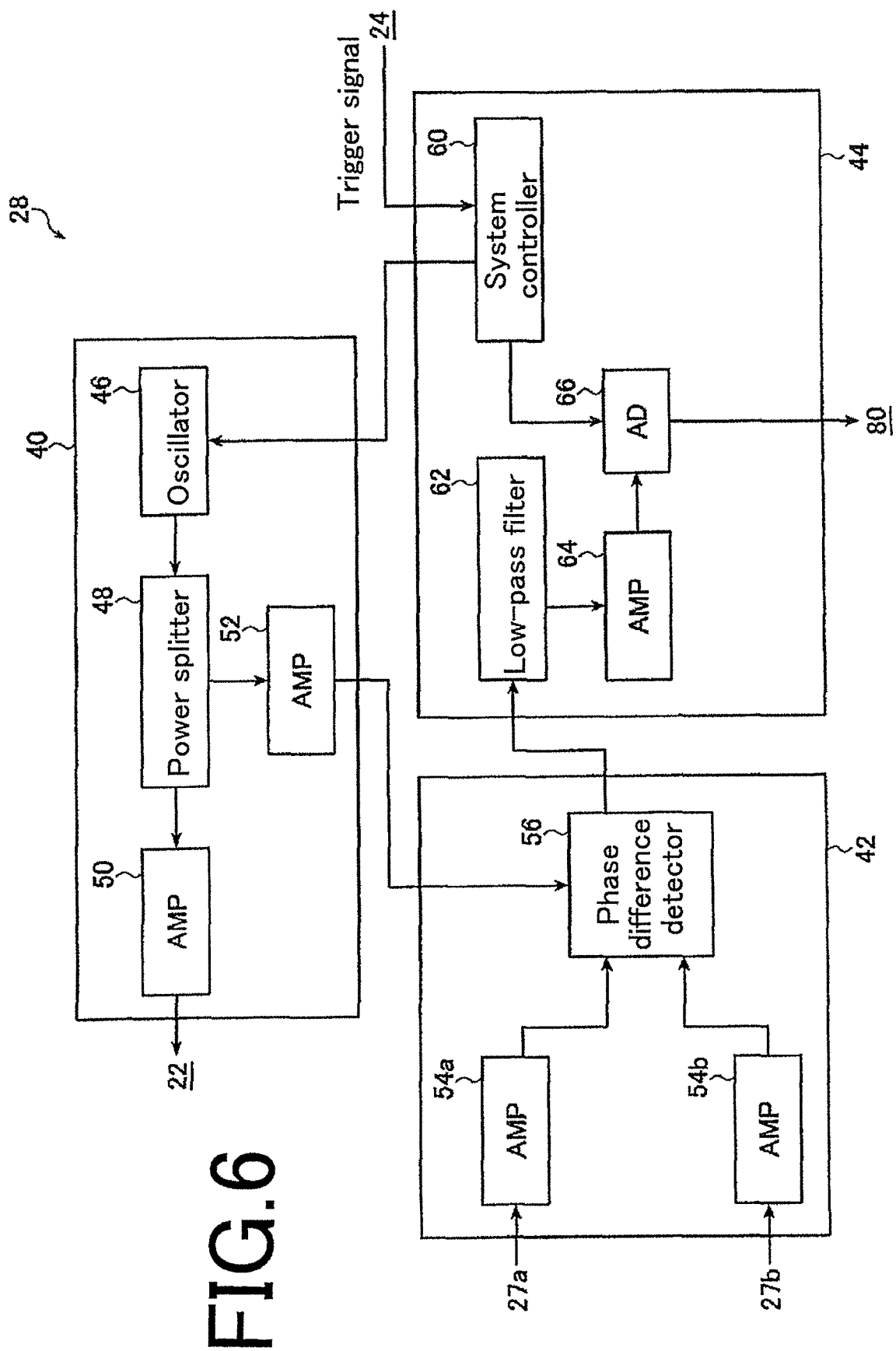
FIG. 6 is a schematic configuration diagram of one example of a control and processing section of the flow cytometer shown in FIG. 1.

As shown in FIG. 6, the control and processing section 28 includes a signal generation unit 40, a signal processing unit 42, and a controller 44. The signal generation unit 40 and the controller 44 constitute a light source control unit that generates a modulation signal having a predetermined frequency.

The signal generation unit 40 is a unit that generates a modulation signal for modulating (amplitude modulating) the intensity of laser light at a predetermined frequency.

More specifically, the signal generation unit 40 includes an oscillator 46, a power splitter 48, and amplifiers 50 and 52, and supplies generated modulation signals to the laser light source unit 22 and also to the signal processing unit 42. As will be described later, the modulation signal is supplied to the signal processing unit 42 and is used as a reference signal for detecting the phase difference of fluorescence signals output from the photoelectric converters 27a and 27b. It is to be noted that the modulation signal is a sinusoidal wave signal having a predetermined frequency. In this case, the frequency is set in the range of 10 to 100 MHz.

The signal processing unit 42 extracts, by using fluorescence signals output from the photoelectric converters 27a and 27b, information about the phase delay (phase difference) of fluorescence emitted from the FRET sample 12 by irradiation with laser light. The signal processing unit 42 includes amplifiers 54a and 54b and a phase difference detector 56 having a power splitter (not shown) and IQ mixers (not shown). The amplifiers 54a and 54b amplify fluorescence signals output from the photoelectric converters 27a and 27b. The power splitter (not shown) splits the modulation signal, which is a sinusoidal wave signal supplied from the signal generation unit 40, into split signals and provides the split signals to the amplified fluorescence signals, respectively. Each of the IQ mixers (not shown) mixes the amplified fluorescence signal with the modulation signal.

One of the IQ mixers (not shown) of the phase difference detector 56 is provided to mix the fluorescence signal supplied from the photoelectric converter 27a with the modulation signal supplied from the signal generation unit 40 as a reference signal. The other IQ mixer (not shown) of the phase difference detector 56 is provided to mix the fluorescence signal supplied from the photoelectric converter 27b with the modulation signal supplied from the signal generation unit 40 as a reference signal. More specifically, each of the IQ mixers multiplies the reference signal by the fluorescence signal (RF signal) to calculate a processing signal including the cos component (real part) and the high-frequency component of the fluorescence signal. Simultaneously, each of the IQ mixers also multiplies a signal, which is obtained by shifting the phase of the reference signal by 90 degrees, by the fluorescence signal to calculate a processing signal including the sin component (imaginary part) and the high-frequency component of the fluorescence signal. The processing signal including the cos component and the processing signal including the sin component are supplied to the controller 44.

The controller 44 is a unit that controls the signal generation unit 40 to generate a sinusoidal wave signal having a predetermined frequency. The controller 44 is also a unit that obtains the cos component and the sin component of the fluorescence signal by removing the high-frequency component from the processing signals which are obtained by the signal processing unit 42 and which include the cos component and the sin component of the fluorescence signal.

More specifically, the controller 44 includes a system controller 60, a low-pass filter 62, an amplifier 64, and an A/D converter 66. The system controller 60 gives instructions for controlling the respective operations of the units and manages all the operations of the flow cytometer 10. The low-pass filter 62 removes the high-frequency component from the processing signal in which the high-frequency component is added to the cos component and from the processing signal in which the high-frequency component is added to the sin component. Here, the processing signals are calculated by the signal processing unit 42. The amplifier 64 amplifies the processing signal including the cos component which is obtained by removing the high-frequency component and the processing signal including the sin component which is obtained by removing the high-frequency component. The A/D converter 66 samples the amplified processing signals. In the A/D converter 66, the processing signal including the cos component which is obtained by removing the high-frequency component and the processing signal including the sin component which is obtained by removing high-frequency component are sampled and then supplied to the analysis device 80.

The analysis device 80 is a device that calculates, from the processing signal values (detection values) of the cos component (real part) and the sin component (imaginary part) of the fluorescence signal, fluorescence intensity information and phase information on each fluorescence component, fluorescence lifetime (fluorescence relaxation time constant), and FRET efficiency. For example, the analysis device 80 calculates the fluorescence intensity $P_d$ and phase $\theta_d$ (measurement values) of fluorescence within the donor wavelength band from a detection value obtained by the photoelectric converter 27a, and calculates the fluorescence intensity $P_a$ and phase $\theta_a$ (measurement values) of fluorescence within the acceptor wavelength band from a detection value obtained by the photoelectric converter 27b. The analysis device 80 corresponds to the FRET detection device according to the present invention and implements a FRET detection method which will be described later.

Figure 7:
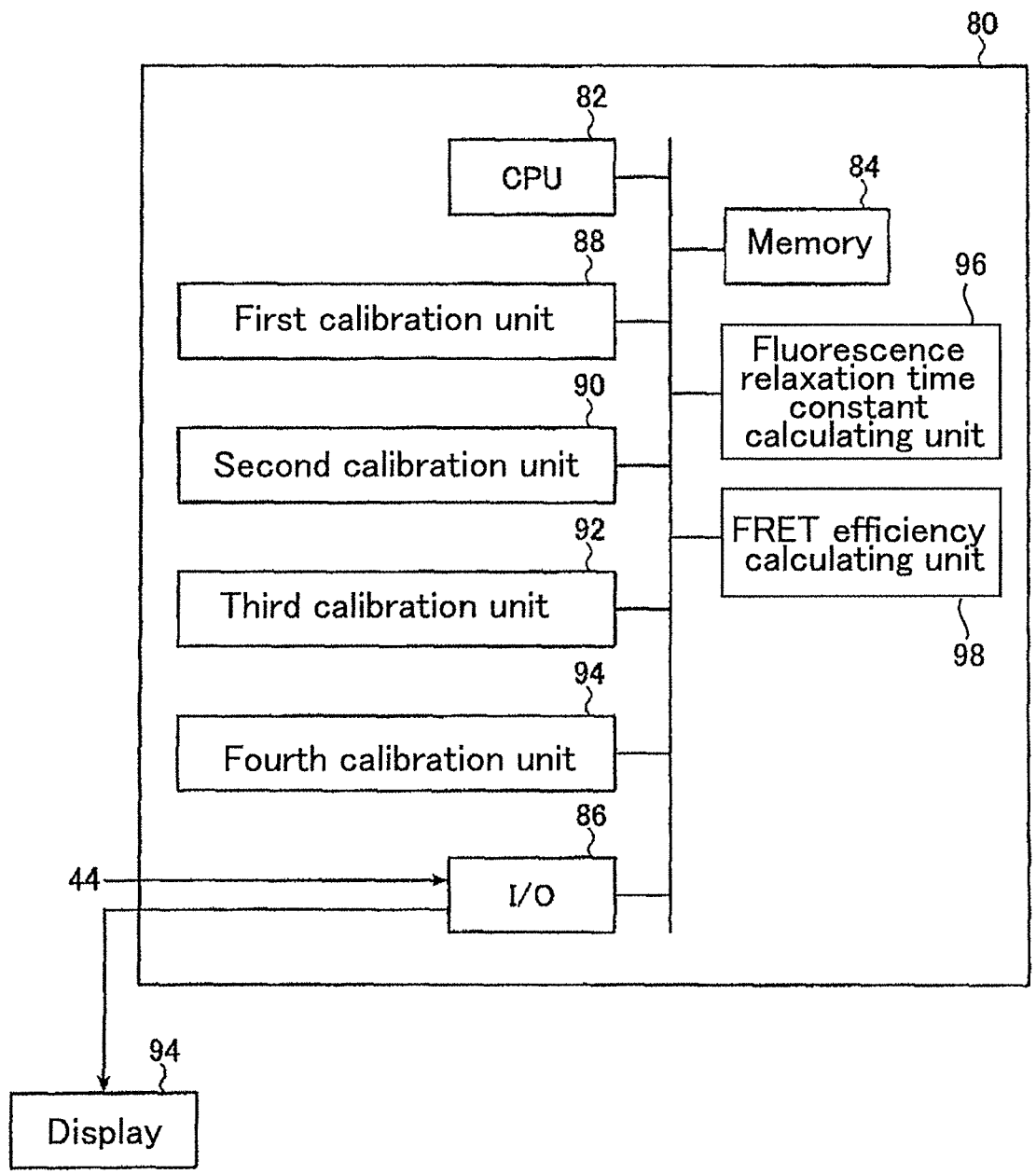
FIG. 7 is a schematic configuration diagram of one example of an analysis device of the flow cytometer shown in FIG. 1.

FIG. 7 is a schematic configuration diagram of the analysis device 80.

The analysis device 80 is a device that is configured to execute a predetermined program on a computer. The analysis device 80 includes, in addition to a CPU 82, a memory 84, and an input/output port 86, a first calibration unit 88, a second calibration unit 90, a third calibration unit 92, a fourth calibration unit 94, a fluorescence relaxation time constant calculating unit 96, and a FRET efficiency calculating unit 98 which are formed by executing software. The analysis device 80 is connected with a display 94.

The CPU 82 is a calculating processor provided in the computer, and substantially executes various calculations required by the first calibration unit 88, the second calibration unit 90, the third calibration unit 92, the fourth calibration unit 94, the fluorescence relaxation time constant calculating unit 96, and the FRET efficiency calculating unit 98. The first calibration unit 88 performs autofluorescence calibration, the second calibration unit 90 performs first molecule calibration, the third calibration unit 92 performs second molecule calibration, and the fourth calibration unit 94 performs non-FRET calibration.

The memory 84 includes a ROM that stores the program executed on the computer to form the first calibration unit 88, the second calibration unit 90, the third calibration unit 92, the fourth calibration unit 94, the fluorescence relaxation time constant calculating unit 96, and the FRET efficiency calculating unit 98 and a RAM that stores processing results calculated by these units and data supplied from the input/output port 86.

The input/output port 86 is used to accept the input of detection values of the cos component (real part) and the sin component (imaginary part) of the fluorescence signal supplied from the controller 44 and also to output information such as the values of processing results calculated by the units 88, 90, 92, 94, 96, and 98 or a scatter diagram onto the display 94. The display 94 displays amplitude information and phase difference information on fluorescence or the values of processing results, such as fluorescence relaxation time constant and FRET efficiency, determined by the units 88, 90, 92, 94, 96, and 98 or a graph such as a scatter diagram.

The fluorescence relaxation time constant calculating unit 96 calculates, from the detection values of the cos component and the sin component supplied from the controller 44, fluorescence intensity information and phase information (information about phase difference) on fluorescence received by each of the photoelectric converters 27a and 27b. Then, a FRET fluorescence lifetime of donor molecule fluorescence component, a FRET fluorescence lifetime of acceptor molecule fluorescence component, and a non-FRET fluorescence lifetime of acceptor molecule fluorescence component are determined using the calculated fluorescence intensity information, the calculated phase information, and calibration information (which will be described later) previously stored in the memory 84. The FRET fluorescence lifetime of donor molecule fluorescence component refers to a fluorescence lifetime of a fluorescence component emitted by the donor molecule excited by laser light at the time when FRET occurs. The FRET fluorescence lifetime of acceptor molecule fluorescence component refers to a fluorescence lifetime of a fluorescence component emitted by the acceptor molecule excited by laser light at the time when FRET occurs. The non-FRET fluorescence lifetime of acceptor molecule fluorescence component refers to a fluorescence lifetime of a fluorescence component emitted by the acceptor molecule excited by laser light at the time when FRET does not occur. Each fluorescence lifetime is expressed as a fluorescence relaxation time constant defined by assuming that all the fluorescence components emitted by the FRET sample 12 irradiated with laser light are based on relaxation responses of first-order lag system. The fluorescence relaxation time constant calculating unit 96 will be described later in detail.

The FRET efficiency calculating unit 98 determines FRET efficiency represented by the ratio between the FRET fluorescence lifetime of donor molecule fluorescence component and a non-FRET fluorescence lifetime of donor molecule fluorescence component, both of the lifetimes determined by the fluorescence relaxation time constant calculating unit 96. The non-FRET fluorescence lifetime of donor molecule fluorescence component is included in the calibration information. The non-FRET fluorescence lifetime of donor molecule fluorescence component refers to a fluorescence lifetime of a fluorescence component emitted by the donor molecule excited by laser light at the time when FRET does not occur.

The FRET efficiency calculating unit 98 may determine FRET efficiency by using the FRET fluorescence lifetime of acceptor molecule fluorescence component and the non-FRET fluorescence lifetime of acceptor molecule fluorescence component determined by the fluorescence relaxation time constant calculating unit 96. In this case, the value of the FRET efficiency is different from that of the above case. The FRET efficiency calculating unit 98 will be described later in detail.

Hereinbelow, the principles of the FRET detection method according to the present invention will be described. As described above, when the FRET sample having the donor molecule and the acceptor molecule is irradiated with laser light to mainly excite the donor molecule and then FRET occurs, the labeled sample emits fluorescence $f_d$, fluorescence $f_f$, fluorescence $f_a$, and fluorescence $f_s$ shown in FIG. 5.

First, consideration is given to a fluorescence emission model, including a non-radiative process, at the time when the FRET sample is excited by an ideal pulse light source with a pulse width of 0. An impulse response (the number of photons emitted per unit volume (fluorescence intensity)) can be represented by the following formula (1). When a fluorescent molecule absorbs light, it takes only $10^{-15}$ second for electrons in the fluorescent molecule to transit to the excited state. Then, after a lapse of $10^{-13}$ to $10^{-11}$ second, the electrons fall from the first excited state by intramolecular relaxation process. Therefore, as in the model represented by the following formula (1), the dynamics of such absorption and intramolecular relaxation processes are neglected, and consideration is herein given to only the process of radiative transition from the first excited state.

[Formula 1]

$$F(t) = k_f N(t) = k_f N_0 e^{-(k_f + k_{nf})t} = \frac{N_0}{\tau_0} e^{-t/\tau} \quad (1)$$

wherein

N(t): number of fluorescent molecules in excited state per unit volume (excited-state density function)

$N_0$: number of fluorescent molecules in excited state at time 0 per unit volume $k_f$: rate constant of radiative transition (ratio of number of molecules undergoing radiative transition per unit time)

$k_{nf}$: rate constant of non-radiative transition (ratio of number of molecules undergoing non-radiative transition per unit time)

$\tau_0 \equiv 1/k_f$: lifetime of excited state defined by assuming that there is no non-radiative process (natural lifetime)

$\tau \equiv 1/(k_f + k_{nf})$: fluorescence relaxation time constant

Here, $N_0$ depends on the molar absorbance coefficient and molar concentration of the fluorescent molecules, and therefore varies depending on the amount of fluorescent molecule label attached (i.e., depending on the amount or state of the donor molecule or the acceptor molecule attached to the cell). It is to be noted that $k_f$ and $k_{nf}$ have a relationship represented by the following formula (2), wherein φ represents the quantum yield of the fluorescent molecule.

[Formula 2]

$$\frac{k_f}{k_f + k_{nr}} = \phi \quad (2)$$

The differential equation of a system whose impulse response is represented by the formula (1) can be represented by the following formula when the incident power of laser is defined as u(t).

[Formula 3]

$$\frac{dN(t)}{dt} = -(k_f + k_{nr})N(t) + N_0 u(t) \quad (3)$$

Based on such an impulse model of fluorescence emission from the fluorescent molecule, consideration is given to a dynamics model of fluorescence emission process of each of the fluorescence components shown in FIG. 5 generated when FRET occurs. When FRET occurs in the FRET sample having the donor molecule and the acceptor molecule, radiative transition, non-radiative transition, and excitation energy transfer proceed concurrently one another in the donor molecule. The model of a fluorescence component within the donor wavelength band emitted by the donor molecule (corresponding to the route $R_1$ shown in FIG. 5) can be represented by the following formulas (4) and (5).

[Formula 4]

$$\frac{dN_d(t)}{dt} = -(k_d + k_t)N_d(t) + N_{d0}u(t) \quad (4)$$

$$F_d(t) = k_{df} N_d(t) \quad (5)$$

On the other hand, the acceptor molecule in the excited state is additionally excited by excitation energy transfer. The model of fluorescence components within the acceptor wavelength band emitted by the acceptor molecule (corresponding to the routes $R_4$ and $R_7$ shown in FIG. 5) can be represented by the following formulas (6) and (7).

[Formula 5]

$$\frac{dN_a(t)}{dt} = k_t N_d(t) - k_a N_a(t) + N_{a0} u(t) \quad (6)$$

$$F_a(t) = k_{af} N_a(t) \quad (7)$$

wherein $N_d(t)$ represents the number of donor fluorescent molecules in the excited state per unit volume, $N_p(t)$ represents the number of acceptor fluorescent molecules in the excited state per unit volume, $k_d$ represents the sum of the rate constant of radiative transition and the rate constant of non-radiative transition of the donor molecule, $k_a$ represents the sum of the rate constant of radiative transition and the rate constant of non-radiative transition of the acceptor molecule, $k_{df}$ represents the rate constant of radiative transition of the donor molecule, $k_{af}$ represents the rate constant of radiative transition of the acceptor molecule, $N_{d0}$ represents the number of donor fluorescent molecules in the excited state at time 0 per unit volume, $N_{a0}$ represents the number of acceptor fluorescent molecules in the excited state at time 0 per unit volume, and $k_t$ represents the rate constant of energy transfer from the donor molecule to the acceptor molecule. It is to be noted that the term $k_t N_d(t)$ in the formula (7) corresponds to the fluorescence component indicated by the route $R_7$ in FIG. 5, which is emitted by the acceptor molecule by FRET.

Further, the model of a fluorescence component within the acceptor wavelength band emitted by the donor molecule (corresponding to the route $R_5$ shown in FIG. 5) can be represented by the following formulas (8) and (9). The model of a fluorescence component within the donor wavelength band emitted by the acceptor molecule (corresponding to the route $R_2$ shown in FIG. 5) can be represented by the following formulas (10) and (11). It is to be noted that in general, it can also be considered that the dynamics of fluorescence of the donor molecule and the dynamics of fluorescence of the acceptor molecule are not changed depending on the wavelength band chosen, but here, it is more generally assumed that the dynamics of fluorescence of the donor molecule and the dynamics of fluorescence of the acceptor molecule are changed depending on the wavelength band chosen.

[Formula 6]

$$\frac{dN_{da}(t)}{dt} = -k_{da} N_{da}(t) + N_{da0} u(t) \quad (8)$$

$$F_{da}(t) = k_{daf} N_{da}(t) \quad (9)$$

-continued $$\frac{dN_{ad}(t)}{dt} = -k_{ad}N_{ad}(t) + N_{ad0}u(t) \quad (10)$$

$$F_{ad}(t) = k_{adf}N_{ad}(t) \quad (11)$$

wherein $N_{da}(t)$ represents the number of donor fluorescent molecules in the excited state per unit volume within the acceptor wavelength band, $N_{ad}(t)$ represents the number of acceptor fluorescent molecules in the excited state per unit volume within the donor wavelength band, $k_{da}$ represents the sum of the rate constant of radiative transition and the rate constant of non-radiative transition of the donor molecule within the acceptor wavelength band, $k_{ad}$ represents the sum of the rate constant of radiative transition and the rate constant of non-radiative transition of the acceptor molecule within the donor wavelength band, $k_{daf}$ represents the rate constant of radiative transition of the donor molecule within the acceptor wavelength band, $k_{adf}$ represents the rate constant of radiative transition of the acceptor molecule within the donor wavelength band, $N_{da0}$ represents the number of donor fluorescent molecules in the excited state at time 0 per unit volume within the acceptor wavelength band, and $N_{ad0}$ represents the number of acceptor fluorescent molecules in the excited state at time 0 per unit volume within the donor wavelength band.

The model of a fluorescence component within the donor wavelength band of autofluorescence emitted by the cell (corresponding to the route $R_3$ shown in FIG. 5) can be represented by the following formulas (12) and (13). The model of a fluorescence component within the acceptor wavelength band of autofluorescence emitted by the cell (corresponding to the route $R_6$ shown in FIG. 5) can be represented by the following formulas (14) and (15). It can be considered that various kinds of molecules contribute to the emission of autofluorescence from the cell, and therefore the model of autofluorescence may be different from the model of a single emission of fluorescence. However, in general, autofluorescence is not strong, and therefore, in the following formulas (12) to (15), the characteristics of the sum of fluorescences emitted by the various kinds of molecules are first-order approximated.

[Formula 7]

$$\frac{dN_{bd}(t)}{dt} = -k_{bd}N_{bd}(t) + N_{bd0}u(t) \quad (12)$$

$$F_{bd}(t) = k_{bdf}N_{bd}(t) \quad (13)$$

$$\frac{dN_{ba}(t)}{dt} = -k_{ba}N_{ba}(t) + N_{ba0}u(t) \quad (14)$$

$$F_{ba}(t) = k_{baf}N_{ba}(t) \quad (15)$$

The above formulas (4) to (15) are subjected to Laplace transform to derive a formula representing fluorescence within the donor wavelength band ($F_{donor}$) and a formula representing fluorescence within the acceptor wavelength band ($F_{acceptor}$). The fluorescence $F_{donor}$ and the fluorescence $F_{acceptor}$ are represented by the following formulas (16) and (17), respectively.

[Formula 8]

$$F_{donor}(s) = \left(\frac{k_{df}N_{d0}\tau_d^*}{1+\tau_d^*s} + \frac{k_{adf}N_{ad0}\tau_{ad}}{1+\tau_{ad}s} + \frac{k_{bdf}N_{bd0}\tau_{bd}}{1+\tau_{bd}s}\right) \cdot U(s) \quad (16)$$

$$F_{acceptor}(s) = \quad (17)$$
$$\left\{k_{af}\left(\frac{k_t\tau_a}{1+\tau_a s} \cdot \frac{N_{d0}\tau_d^*}{1+\tau_d^*s} + \frac{N_{a0}\tau_a}{1+\tau_a s}\right) + \frac{k_{daf}N_{da0}\tau_{da}}{1+\tau_{da}s} + \frac{k_{baf}N_{ba0}\tau_{ba}}{1+\tau_{ba}s}\right\} \cdot U(s)$$

wherein $\tau_d^*$: fluorescence relaxation time constant of donor molecule at the time when FRET occurs=$1/(k_d+k_t)$ ($k_t=0$ (non-FRET state), $\tau_d^*=\tau_d=1/k_d$)

Figure 8:
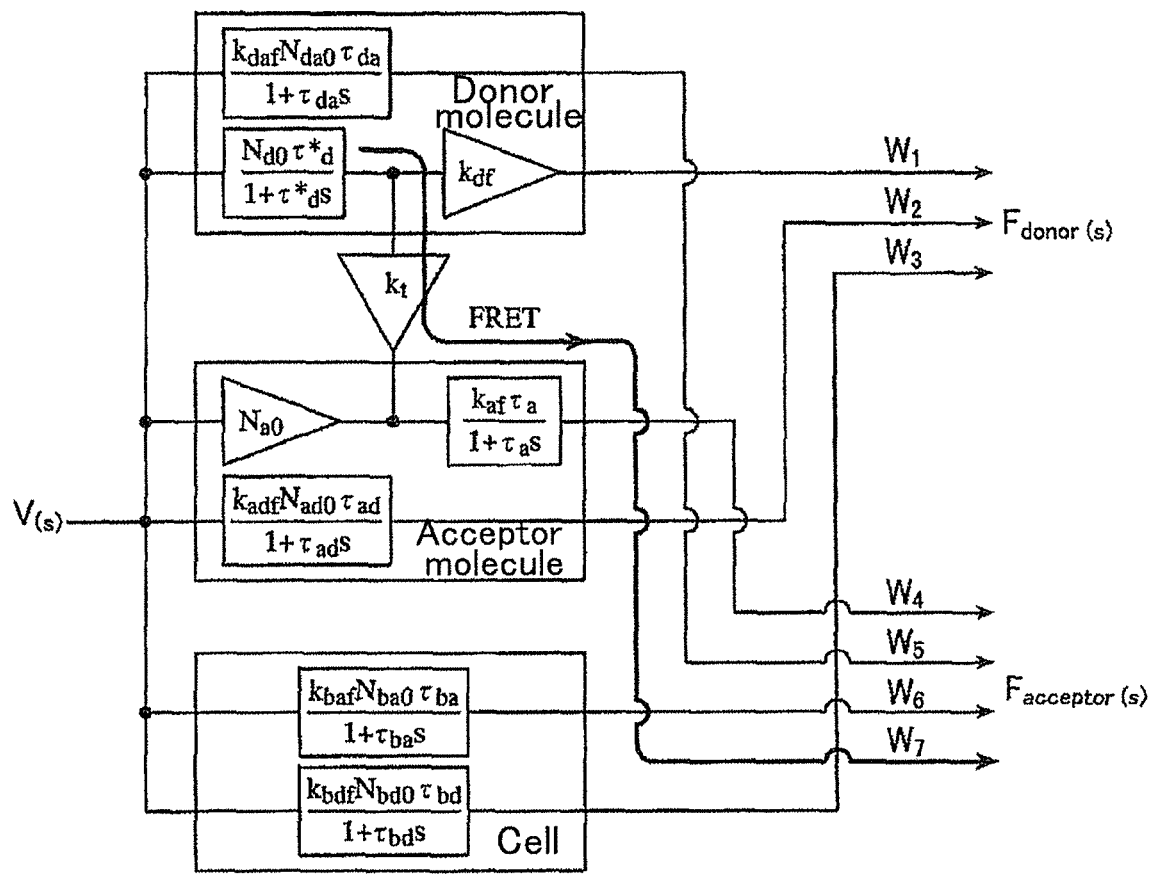
FIG. 8 is a diagram illustrating a model of dynamics of fluorescence emission at the time when FRET occurs.

$\tau_a$: fluorescence relaxation time constant of acceptor molecule=$1/k_a$ $\tau_{ad}$: fluorescence relaxation time constant of acceptor molecule within donor wavelength band=$1/k_{ad}$ $\tau_{da}$: fluorescence relaxation time constant of donor molecule within acceptor wavelength band=$1/k_{da}$ $\tau_{bd}$: fluorescence relaxation time constant of autofluorescence of cell within donor wavelength band=$1/k_{bd}$ $\tau_{ba}$: fluorescence relaxation time constant of autofluorescence of cell within acceptor wavelength band=$1/k_{ba}$ FIG. 8 is a diagram illustrating a model of dynamics of fluorescence emission at the time when FRET occurs, which is represented by the formulas (16) and (17). It can be considered that the FRET sample 12 emits fluorescence components indicated by routes $W_1$ to $W_7$ in FIG. 8. In the present invention, it can be considered that these fluorescence components indicated by the routes $W_1$ to $W_7$ in the model shown in FIG. 8 correspond to the fluorescence components ($R_1$ to $R_7$) introduced into the photoelectric converters 27a and 27b shown in FIG. 4, respectively.

In the device 10, laser light output which is emitted from the laser light source unit 22 is changed (modulated) into a sinusoidal wave at high speed to irradiate the sample, and a fluorescence intensity signal output from the sample is processed at high speed to detect an amplitude (fluorescence intensity information) and a phase (phase information) per cell. That is, frequency response characteristics of transfer functions given by the formulas (16) and (17) are detected. When a fluorescence signal is measured under the condition that a sinusoidal wave with an angular frequency $\omega_M$ is applied to the power u(t) of laser, the fluorescent signal is output as a sinusoidal wave having the same angular frequency. The amplitude ratio and phase difference between an input signal and an output signal can be expressed as the sum of vectors in a complex plane when s in the formulas (16) and (17) is defined as $j\omega_M$ and can be represented by the following formulas (18) and (19).

[Formula 9]

$$\frac{F_{donor}(s)}{U(s)} = P_1 e^{j\theta_1} + P_2 e^{j\theta_2} + P_3 e^{j\theta_3} \quad (18)$$

-continued $$\frac{F_{acceptor}(s)}{U(s)} = P_7 e^{j\theta_7} + P_4 e^{j\theta_4} + P_5 e^{j\theta_5} + P_6 e^{j\theta_6} \quad (19)$$

$$P_1 = \frac{k_{df} N_{d0} \tau_d^*}{\sqrt{1+(\tau_d^* \omega_M)^2}}, \quad \theta_1 = -\tan^{-1} \tau_d^* \omega_M$$

$$P_2 = \frac{k_{adf} N_{ad0} \tau_{ad}}{\sqrt{1+(\tau_{ad} \omega_M)^2}}, \quad \theta_2 = -\tan^{-1} \tau_{ad} \omega_M$$

$$P_3 = \frac{k_{bdf} N_{bd0} \tau_{bd}}{\sqrt{1+(\tau_{bd} \omega_M)^2}}, \quad \theta_3 = -\tan^{-1} \tau_{bd} \omega_M$$

$$P_7 = k_{af} \frac{k_t \tau_a}{\sqrt{1+(\tau_a \omega_M)^2}} \frac{N_{d0} \tau_d^*}{\sqrt{1+(\tau_d^* \omega_M)^2}},$$

$$\theta_7 = -(\tan^{-1} \tau_a \omega_M + \tan^{-1} \tau_d^* \omega_M) = -\tan^{-1} \frac{(\tau_a + \tau_d^*)\omega_M}{1 - \tau_a \tau_d^* \omega_M^2}$$

$$P_4 = \frac{k_{af} N_{a0} \tau_a}{\sqrt{1+(\tau_a \omega_M)^2}}, \quad \theta_4 = -\tan^{-1} \tau_a \omega_M$$

$$P_5 = \frac{k_{daf} N_{da0} \tau_{da}}{\sqrt{1+(\tau_{da} \omega_M)^2}}, \quad \theta_5 = -\tan^{-1} \tau_{da} \omega_M$$

$$P_6 = \frac{k_{baf} N_{ba0} \tau_{ba}}{\sqrt{1+(\tau_{ba} \omega_M)^2}}, \quad \theta_6 = -\tan^{-1} \tau_{ba} \omega_M$$

It goes without saying that the first term, second term, and third term of the formula (18) correspond to $W_1$, $W_2$, and $W_3$ in FIG. 8, respectively, and that the first term, second term, third term, and fourth term of the formula (19) correspond to $W_7$ (FRET component), $W_4$, $W_5$, and $W_6$ in FIG. 8, respectively.

It is difficult for conventional methods to quantitatively determine the fluorescence relaxation time constant $\tau_d^*$ of a donor molecule at the time when FRET occurs or the equivalent fluorescence relaxation time constant $\tau_a^*$ (=$\tan \theta_7/\omega_M$) of an acceptor molecule at the time when FRET occurs. If $\tau_d^*$ and $\tau_a^*$ can be quantitatively determined, it is possible to detect the occurrence of FRET with a high degree of accuracy. As can be seen from the above relationships, $\tau_d^*$ can be determined by determining $P_1$ and $\theta_1$, and $\tau_a^*$ can be determined by determining the above $P_7$ and $\theta_7$.

Here, when the fluorescence intensity and phase of fluorescence within the donor wavelength band (including $W_1$ to $W_3$ shown in FIG. 8) are defined as $P_{donor}$ and $\theta_{donor}$, respectively, the formula (18) can be transformed into the following formula (20). As can be seen from the formula (20), $P_1$ and $\theta_1$ can be determined when the intensity $P_{donor}$ and phase $\theta_{donor}$ of fluorescence within the donor wavelength band (including $W_1$ to $W_3$ shown in FIG. 8), $P_2/P_4$, $P_4$, $P_3$, and $\theta_3$ are known.

[Formula 10]

$$P_1 e^{j\theta_1} = P_{donor} e^{j\theta_{donor}} - P_2 e^{j\theta_2} - P_3 e^{j\theta_3} \quad (20)$$

$$= P_{donor} e^{j\theta_{donor}} - \frac{P_2}{P_4} P_4 e^{j\theta_2} - P_3 e^{j\theta_3}$$

Further, when the fluorescence intensity and phase of fluorescence within the acceptor wavelength band (including $W_4$ to $W_7$ shown in FIG. 8) are defined as $P_{acceptor}$ and $\theta_{acceptor}$, respectively, the formula (19) can be transformed into the following formula (21). As can be seen from the formula (21), $P_7$ and $\theta_7$ can be determined when the intensity $P_{acceptor}$ and phase $\theta_{acceptor}$ of fluorescence within the acceptor wavelength band, $P_5/P_1$, $P_1$, $P_6$, and $\theta_6$ are known.

[Formula 11]

$$P_7 e^{j\theta_7} = P_{acceptor} e^{j\theta_{acceptor}} - P_4 e^{j\theta_4} - P_5 e^{j\theta_5} - P_6 e^{j\theta_6} \quad (21)$$

$$= P_{acceptor} e^{j\theta_{acceptor}} - P_4 e^{j\theta_4} - \frac{P_5}{P_1} P_1 e^{j\theta_5} - P_6 e^{j\theta_6}$$

In the fluorescence relaxation time constant calculating unit 96 of the analysis device 80, when the sample labeled with the donor molecule and the acceptor molecule is irradiated with the above-mentioned laser light, the fluorescence intensity $P_d$ and phase $\theta_d$ of fluorescence within the donor wavelength band (including $R_1$ to $R_3$ shown in FIG. 5) and the fluorescence intensity $P_a$ and phase $\theta_a$ of fluorescence within the acceptor wavelength band (including $R_4$ to $R_7$ shown in FIG. 5) are first calculated from the above-mentioned cos component and sin component. The measured values $P_d$ and $\theta_d$ correspond to the above-mentioned $P_{donor}$ and $\theta_{donor}$, respectively, and $P_a$ and $\theta_a$ likewise correspond to the above-mentioned $P_{acceptor}$ and $\theta_{acceptor}$, respectively. The memory 84 of the analysis device 80 stores values corresponding to the above-mentioned $P_2/P_4$, $P_3$ and $\theta_3$, $P_6$ and $\theta_6$, and $P_4$ calculated by the first calibration unit 88 to the fourth calibration unit 94 (which will be described later). Therefore, $P_1$ and $\theta_1$ or $P_7$ and $\theta_7$ are calculated using these values, and then $\tau_d^*$, $\tau_a^*$, and $\tau_a$, that is, the FRET fluorescence lifetime of donor molecule fluorescence component, the FRET fluorescence lifetime of acceptor molecule fluorescence component, and the non-FRET fluorescence lifetime of acceptor molecule fluorescence component are determined from the definitional formulas of $P_i$ and $\theta_i$ (i is an integer of 1 to 7) associated with the formulas (18) and (19) and the definitional formula $\tau_a^* = \tan \theta_7/\omega_M$. At this time, the fluorescence relaxation time constant calculating unit 96 converts a formula expressed by phases and amplitudes, such as the formula (20) or (21), into a vector to perform vector operation.

The FRET efficiency calculating unit 98 determines FRET efficiency $E_t$ defined by the following formula (22) by using the fluorescence relaxation time constant $\tau_d$ of a fluorescence component within the donor wavelength band emitted by the donor molecule (corresponding to the route $R_1$ shown in FIG. 4 in the non-FRET state). It is to be noted that the fluorescence relaxation time constant $\tau_d$ is previously determined by, for example, the second calibration unit 90 and the fourth calibration unit 94 (which will be described later) and stored in the memory 84.

[Formula 12]

$$E_t = 1 - \tau_d^*/\tau_d \quad (22)$$

The fluorescence relaxation time constant of the donor molecule is shorter when the degree of FRET is higher, that is, when energy transferred from the donor molecule to the acceptor molecule is larger. Such FRET efficiency $E_t$ represents the degree of transfer of energy from the donor molecule to the acceptor molecule (the degree of FRET).

Further, in the present invention, FRET can be quantitatively measured also from measurement results within the acceptor wavelength band. In this case, as the fluorescence relaxation time constant $\tau_a$, a value stored in the memory 84 can of course be used. The fluorescence relaxation time constant $\tau_a$ is previously determined by, for example, the third calibration unit 92 and the fourth calibration unit 94 (which will be described later) and stored, and this value may be used.

By determining the fluorescence relaxation time constant $\tau_d^*$ of the donor molecule at the time when FRET occurs from the fluorescence relaxation time constants $\tau_a$ and $\tau_a^*$ of the acceptor molecule with the use of the following formula (23), it is possible to multilaterally determine information on fluorescence relaxation time constant at the time when FRET occurs not only from measurement results within the donor wavelength band but also from measurement results within the acceptor wavelength band.

[Formula 13]

$$\tau_a^* \equiv \tan\theta_t / \omega_M = \frac{\tau_a + \tau_d^*}{1 - \tau_a \tau_d^* \omega_M^2} \quad (23)$$

Hereinbelow, each of the first calibration unit 88 to the fourth calibration unit 94 will be described. When a sample, such as a cell, which has no fluorochrome attached thereto and which emits autofluorescence is defined as an unlabeled sample, the first calibration unit 88 calculates fluorescence intensity information and phase information on autofluorescence emitted by the unlabeled sample. The first calibration unit 88 acquires detection values including phase information from each of the photoelectric converters when the unlabeled sample as a measuring object is irradiated with laser light whose intensity is modulated at a predetermined frequency, and calculates fluorescence intensity information and phase information from these detection values.

Figure 9:
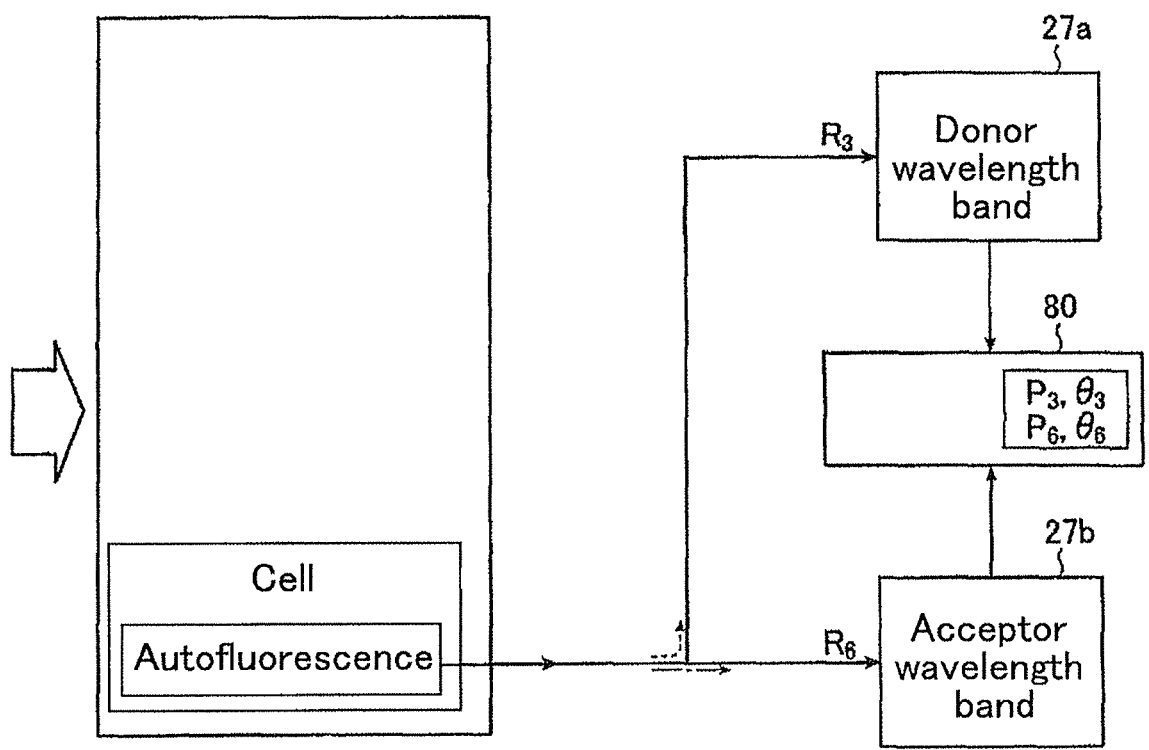
FIG. 9 is a diagram illustrating the components of fluorescence emitted by an unlabeled sample and the incidence of these fluorescence components into photoelectric converters in the flow cytometer shown in FIG. 1.

More specifically, as shown in FIG. 9, the first calibration unit 88 calculates, when the unlabeled sample (e.g., cell) is irradiated with laser light, fluorescence intensity information and phase information on fluorescence within the donor wavelength band emitted by the cell itself and on fluorescence within the acceptor wavelength band emitted by the cell itself. Here, it can be assumed that fluorescence emitted by the cell itself is not influenced by labels such as a donor molecule and an acceptor molecule. More specifically, a measured value $P_{md1}$ of fluorescence intensity of autofluorescence within the donor wavelength band and a measured value $\theta_{md1}$ of phase of autofluorescence within the donor wavelength band obtained by the first calibration unit 88 are information on a fluorescence component indicated by $R_3$ in FIG. 5. A measured value $P_{ma1}$ of fluorescence intensity of autofluorescence within the acceptor wavelength band and a measured value $\theta_{ma1}$ of phase difference of autofluorescence within the acceptor wavelength band are information on a fluorescence component indicated by $R_6$ in FIG. 5. These measured values can be directly used for the model of process of FRET occurrence shown in FIG. 8, and relationships represented by the following formulas (24) and (25) are established. The thus determined $P_3$ and $\theta_3$ and $P_6$ and $\theta_6$ are stored in the memory 84.

[Formula 14]

$$P_3 e^{j\theta_3} = P_{md1} e^{j\theta_{md1}} \quad (24)$$

$$P_6 e^{j\theta_6} = P_{ma1} e^{j\theta_{ma1}} \quad (25)$$

The second calibration unit 90 calculates the fluorescence intensity and phase of fluorescence emitted by a donor-labeled sample having only a donor fluorochrome. Further, the second calibration unit 90 calculates the ratio of the fluorescence intensity of a fluorescence component within the acceptor wavelength band to the fluorescence intensity of a fluorescence component within the donor wavelength band (leak rate of donor fluorescence) by using the calculated information on the fluorescence intensity and phase of the donor-labeled sample and the values of fluorescence intensity and phase of fluorescence components emitted by the unlabeled sample ($P_3$ and $\theta_3$ and $P_6$ and $\theta_6$) calculated by the first calibration unit.

Figure 10:
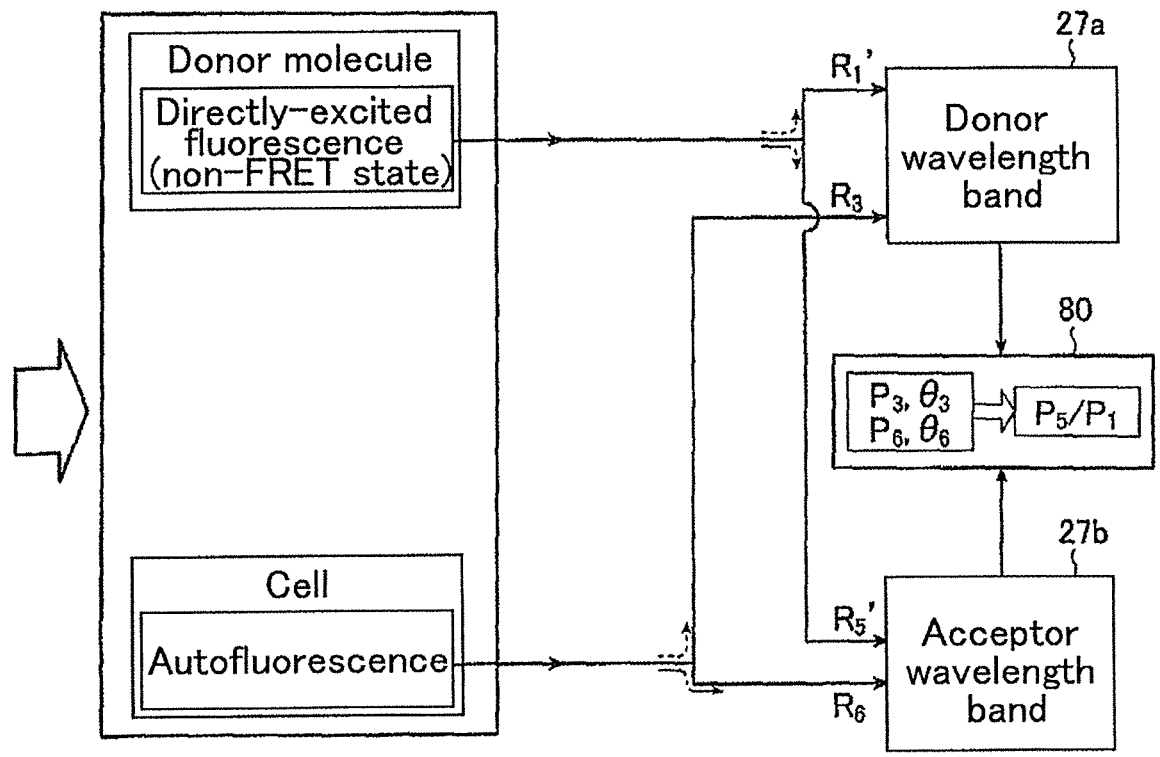
FIG. 10 is a diagram illustrating the components of fluorescence emitted by a donor-labeled sample and the incidence of these fluorescence components into photoelectric converters in the flow cytometer shown in FIG. 1.

More specifically, as shown in FIG. 10, the second calibration unit 90 calculates, when the donor-labeled sample is irradiated with laser light, the fluorescence intensity and phase of fluorescence within the donor wavelength band emitted by the donor molecule and the cell itself and those of fluorescence within the acceptor wavelength, band emitted by the donor molecule and the cell itself. Here, when the measured value of fluorescence intensity of the fluorescence within the donor wavelength band, the measured value of phase difference of the fluorescence within the donor wavelength band, the measured value of fluorescence intensity of the fluorescence within the acceptor wavelength band, and the measured value of phase difference of the fluorescence within the acceptor wavelength band obtained by the second calibration unit 90 are defined as $P_{md2}$, $\theta_{md2}$, $P_{ma2}$, and $\theta_{ma2}$, respectively, the fluorescence intensity and phase of fluorescence (indicated by $R_1'$ in FIG. 10) within the donor wavelength band emitted by the donor molecule of the donor-labeled sample are defined as $P_1'$ and $\theta_1'$, respectively, and the fluorescence intensity and phase of fluorescence (indicated by $R_5'$ in FIG. 10) within the acceptor wavelength band emitted by the donor molecule of the donor-labeled sample are defined as $P_5'$ and $\theta_5'$, respectively, relationships represented by the following formulas (26) and (27) are established. As described above, as the values of the fluorescence intensity and phase of fluorescence components of autofluorescence, the above-mentioned values calculated by the first calibration unit can be directly used.

[Formula 15]

$$P_1' e^{j\theta_1'} = P_{md2} e^{j\theta_{md2}} - P_3 e^{j\theta_3} \quad (26)$$

$$P_5' e^{j\theta_5'} = P_{ma2} e^{j\theta_{ma2}} - P_6 e^{j\theta_6} \quad (27)$$

The second calibration unit 90 reads, from the memory 84, $P_3$ and $\theta_3$ and $P_6$ and $\theta_6$, which have been calculated by the first calibration unit 88, to calculate $P_1'$ and $\theta_1'$ and $P_5'$ and $\theta_5'$ by using the relationships represented by the formulas (26) and (27). The second calibration unit 90 may also determine, from these results, the fluorescence relaxation time constant $\tau_d$ of fluorescence within the donor wavelength band emitted by the donor molecule at the time when FRET does not occur and the fluorescence relaxation time constant $\tau_{da}$ of fluorescence within the acceptor wavelength band emitted by the donor molecule at the time when FRET does not occur.

As described above, when FRET occurs, radiative transition, non-radiative transition, and excitation energy transfer proceed at the same time in the donor molecule. Further, when the amount of label attached changes, fluorescence intensity also changes, and therefore $P_1'$ and $\theta_1'$ and $P_5'$ and $\theta_5'$ cannot be regarded as information on fluorescence components indicated by $R_1$ and $R_5$ in FIG. 5 and these measured values cannot be directly used for the model of process of FRET occurrence shown in FIG. 8. However, it can be assumed that the ratio between the fluorescence intensity of fluorescence within the donor wavelength band emitted by the donor molecule and the fluorescence intensity of fluorescence within the acceptor wavelength band emitted by the donor molecule, that is, $P_5'/P_1'$ (leak rate of donor fluorescence) is constant among different samples. More specifically, the ratio of $P_5$ to $P_1$ in the formulas (20) and (21) can be represented as follows: $P_5/P_1 = P_5'/P_1'$. The ratio $P_5'/P_1'$ (hereinafter, referred to as $P_5/P_1$) calculated by the second calibration unit 90 is stored in the memory 84. It is to be noted that at this time, $P_1'$ and $\theta_1'$, $P_5'$ and $\theta_5'$, the fluorescence relaxation time constant $\tau_d$ of fluorescence within the donor wavelength band emitted by the donor molecule at the time when FRET does not occur, and the fluorescence relaxation time constant $\tau_{da}$ of fluorescence within the acceptor wavelength band emitted by the donor molecule at the time when FRET does not occur are also stored in the memory 84.

The third calibration unit 92 calculates the fluorescence intensity and phase of fluorescence emitted by a donor-labeled sample having only an acceptor fluorochrome. Further, the third calibration unit 92 calculates the ratio of the fluorescence intensity of a fluorescence component within the donor wavelength band to the fluorescence intensity of a fluorescence component within the acceptor wavelength band (leak rate of acceptor fluorescence) by using the calculated information on the fluorescence intensity and phase of the acceptor-labeled sample and the values of fluorescence intensity and phase ($P_3$ and $\theta_3$ and $P_6$ and $\theta_6$) of fluorescence components emitted by the unlabeled sample calculated by the first calibration unit.

Figure 11:
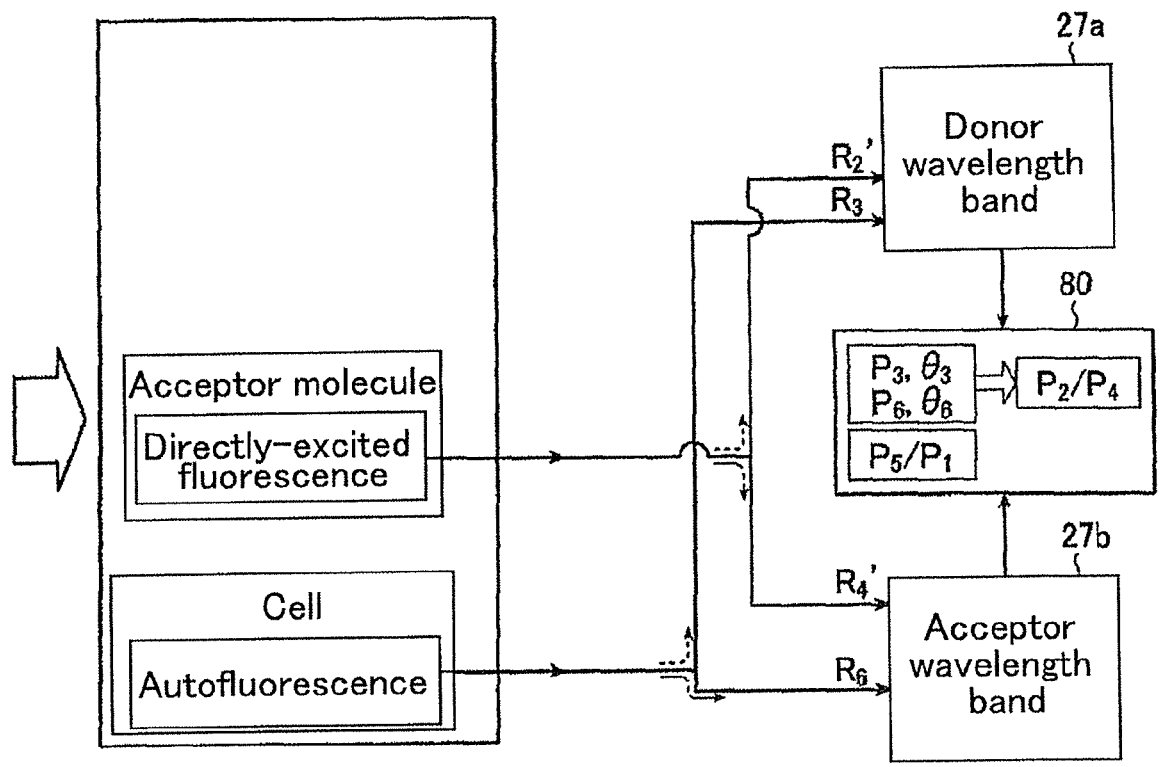
FIG. 11 is a diagram illustrating the components of fluorescence emitted by an acceptor-labeled sample and the incidence of these fluorescence components into photoelectric converters in the flow cytometer shown in FIG. 1.

More specifically, as shown in FIG. 11, the third calibration unit 92 calculates, when the acceptor-labeled sample is irradiated with laser light, the fluorescence intensity and phase of fluorescence within the donor wavelength band emitted by the acceptor molecule and the cell itself and those of fluorescence within the acceptor wavelength band emitted by the acceptor molecule and the cell itself. When the measured value of the fluorescence intensity of the fluorescence within the donor wavelength band, the measured value of phase difference of the fluorescence within the donor wavelength band, the measured value of fluorescence intensity of the fluorescence within the acceptor wavelength band, and the measured value of phase difference of the fluorescence within the acceptor wavelength band obtained by the third calibration unit 90 are defined as $P_{md3}$, $\theta_{md3}$, $P_{ma3}$, and $\theta_{ma3}$, respectively, the fluorescence intensity and phase of fluorescence (indicated by $R_2'$ in FIG. 11) within the donor wavelength band emitted by the acceptor molecule of the acceptor-labeled sample are defined as $P_2'$ and $\theta_2'$, respectively, and the fluorescence intensity and phase of fluorescence (indicated by $R_4'$ in FIG. 11) within the donor wavelength band emitted by the acceptor molecule of the acceptor-labeled sample are defined as $P_4'$ and $\theta_4'$, respectively, relationships represented by the following formulas (28) and (29) are established. As described above, as the values of fluorescence intensity and phase of fluorescence components of autofluorescence, the above-mentioned values calculated by the first calibration unit can be directly used.

[Formula 16]

$$P_2'e^{j\theta_2'} = P_{md3}e^{j\theta_{md3}} - P_3 e^{j\theta_3} \quad (28)$$

$$P_4'e^{j\theta_4'} = P_{ma3}e^{j\theta_{ma3}} - P_6 e^{j\theta_6} \quad (29)$$

The third calibration unit 92 reads, from the memory 84, $P_3$ and $\theta_3$ and $P_6$ and $\theta_6$, which have been calculated by the first calibration unit 88, to calculate $P_2'$ and $\theta_2'$ and $P_4'$ and $\theta_4'$ by using relationships represented by the following formulas (30) and (31). The third calibration unit 92 may also determine, from these results, the fluorescence relaxation time constant $\tau_a$ of fluorescence within the acceptor wavelength band emitted by the acceptor molecule at the time when FRET does not occur and the fluorescence relaxation time constant $\tau_{ad}$ of fluorescence within the donor wavelength band emitted by the acceptor molecule at the time when FRET does not occur. As described above, when the amount of label attached changes, the fluorescence intensity also changes, and therefore $P_2'$ and $\theta_2'$ and $P_4'$ and $\theta_4'$ cannot be applied to the model for the occurrence of FRET shown in FIG. 8. However, it can be assumed that the ratio between the fluorescence intensity of fluorescence within the acceptor wavelength band emitted by the acceptor molecule and the fluorescence intensity of fluorescence within the donor wavelength band emitted by the acceptor molecule, that is, $P_2'/P_4'$ (leak rate of acceptor fluorescence) is constant among different samples. More specifically, the ratio of $P_2$ to $P_4$ in the formulas (20) and (21) can be represented as follows: $P_2/P_4 = P_2'/P_4'$. The ratio $P_2'/P_4'$ (hereinafter, referred to as $P_2/P_4$) calculated by the third calibration unit 92 is stored in the memory 84. It is to be noted that at this time, $P_2'$ and $\theta_2'$, $P_4'$ and $\theta_4'$, and the fluorescence relaxation time constant $\tau_a$ of fluorescence within the acceptor wavelength band emitted by the acceptor molecule at the time when FRET does not occur and the fluorescence relaxation time constant $\tau_{ad}$ of fluorescence within the donor wavelength band emitted by the acceptor molecule at the time when FRET does not occur are also stored in the memory 84.

The fourth calibration unit 94 calculates information on the fluorescence intensity and phase of fluorescence emitted by a non-FRET sample which has both a donor fluorescent molecule and an acceptor fluorescent molecule and which has been treated so as not to cause FRET by, for example, introducing a factor inactivating protein structural change or protein linkage. Further, the fourth calibration unit 94 calculates the fluorescence intensity (represented by $P_4''$ in the following formula (31)) and phase (represented by $\theta_4''$ in the following formula (31)) of fluorescence emitted by the acceptor-labeled sample directly excited by irradiation with laser light by using the calculated information on the fluorescence intensity and phase of fluorescence emitted by the non-FRET sample, the values of fluorescence intensity and phase of fluorescence components emitted by the unlabeled sample ($P_3$ and $\theta_3$ and $P_6$ and $\theta_6$) calculated by the first calibration unit, the leak rate of donor fluorescence ($P_5/P_1$) calculated by the second calibration unit 90, and the leak rate of acceptor fluorescence ($P_2/P_4$) calculated by the third calibration unit 92.

Figure 12:
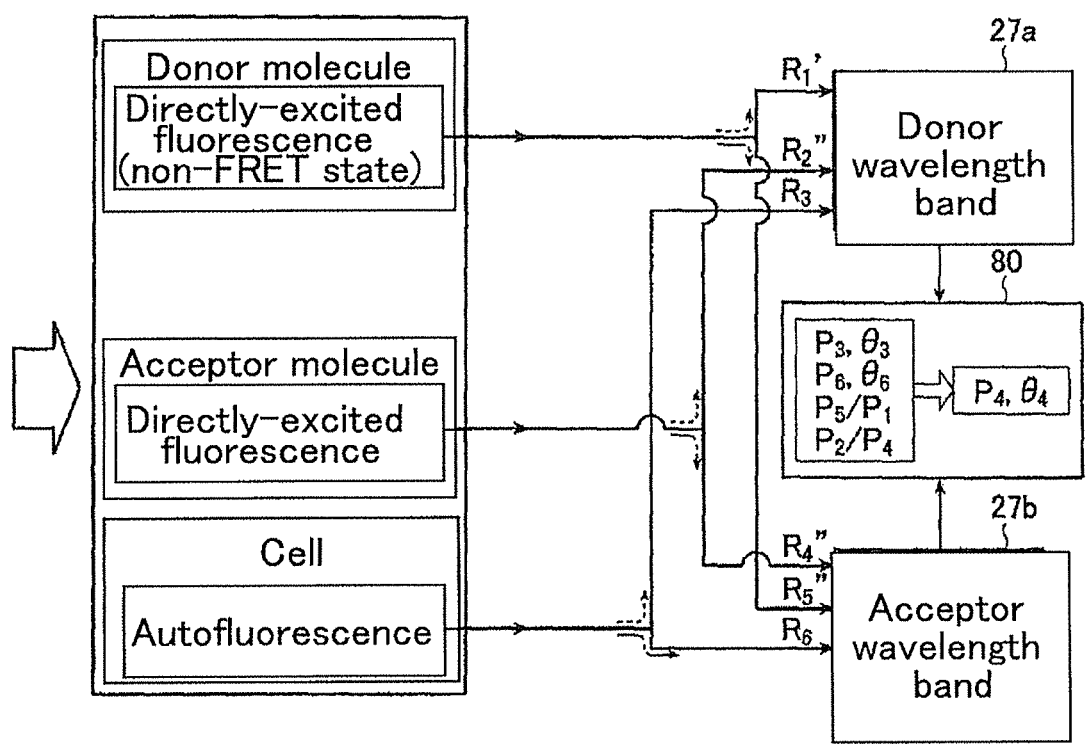
FIG. 12 is a diagram illustrating the components of fluorescence emitted by a non-FRET labeled sample and the incidence of these fluorescence components into photoelectric converters in the flow cytometer shown in FIG. 1.

More specifically, as shown in FIG. 12, the fourth calibration unit 94 calculates, when the non-FRET sample is irradiated with laser light, the fluorescence intensity and phase of fluorescence within the donor wavelength band emitted by the donor and acceptor molecules of the non-FRET sample and the cell itself and the fluorescence intensity and phase of fluorescence within the acceptor wavelength band emitted by the donor and acceptor molecules of the non-FRET sample and the cell itself, that is, $P_1''$, $\theta_1''$, $P_4''$, and $\theta_4''$ in the following formulas (30) and (31). When the measured value of fluorescence intensity of the fluorescence within the donor wavelength band, the measured value of phase difference of the fluorescence within the donor wavelength band, the measured value of fluorescence intensity of the fluorescence within the acceptor wavelength band, and the measured value of phase difference of the fluorescence within the acceptor wavelength band are defined as $P_{md4}$, $\theta_{md4}$, $P_{ma4}$, and $\theta_{ma4}$, respectively, the fluorescence intensity and phase of fluorescence (indicated by $R_1''$ in FIG. 12) within the donor wavelength band emitted by the donor molecule of the non-FRET sample are defined as $P_1''$ and $\theta_1''$, respectively, the fluorescence intensity and phase of fluorescence (indicated by $R_2''$ in FIG. 12) within the donor wavelength band emitted by the acceptor molecule of the non-FRET sample are defined as $P_2''$ and $\theta_2''$, respectively, the fluorescence intensity and phase of fluorescence (indicated by $R_5''$ in FIG. 12) within the acceptor wavelength band emitted by the donor molecule of the non- FRET sample are defined as $P_5''$ and $\theta_5''$, respectively, and the fluorescence intensity and phase of fluorescence (indicated by $R_4''$ in FIG. 12) within the acceptor wavelength band emitted by the acceptor molecule of the non-FRET sample are defined as $P_4''$ and $\theta_4''$, respectively, relationships represented by the following formulas (30) and (31) are established. As described above, as the values of fluorescence intensity and phase of fluorescence components of autofluorescence, the above-mentioned values calculated by the first calibration unit can be directly used.

[Formula 17]

$$P_1'' e^{j\theta_1''} = P_{md4} e^{j\theta_{md4}} - P_2'' e^{j\theta_2''} - P_3 e^{j\theta_3} \quad (30)$$
$$= P_{md4} e^{j\theta_{md4}} - \frac{P_2''}{P_4''} P_4'' e^{j\theta_2''} - P_3 e^{j\theta_3}$$

$$P_4'' e^{j\theta_4''} = P_{ma4} e^{j\theta_{ma4}} - P_5'' e^{j\theta_5''} - P_6 e^{j\theta_6} \quad (31)$$
$$= P_{ma4} e^{j\theta_{ma4}} - \frac{P_5''}{P_1''} P_1'' e^{j\theta_5''} - P_6 e^{j\theta_6}$$

As described above, as the ratio $P_5''/P_1''$ in the formula (31), the leak rate of donor fluorescence ($P_5/P_1$) calculated by the second calibration unit 90 can be directly used (this is because the leak rate of donor fluorescence does not change depending on the amount of label attached). Likewise, as described above, as the ratio $P_2''/P_4''$ in the formula (30), the leak rate of acceptor fluorescence ($P_2/P_4$) calculated by the third calibration unit 92 can be directly used. The fourth calibration unit 94 reads, from the memory 84, $P_3$ and $\theta_3$ and $P_6$ and $\theta_6$ which have been calculated by the first calibration unit 88, $P_5''/P_1''$ which has been calculated by the second calibration unit 90, and $P_2''/P_4''$ which has been calculated by the third calibration unit 92 to calculate $P_4''$ and $\theta_4''$ by using the relationships represented by the formulas (30) and (31). At the same time, $P_1''$ and $\theta_1''$ are also calculated. As $\theta_2''$, $\theta_2'$ calculated by the third calibration unit is used. As $\theta_5''$, $\theta_5'$ calculated by the second calibration unit is used. It is to be noted that the formulas (30) and (31) interact with each other through $P_1''$ and $P_4''$, but since the values of $P_5''/P_1''$ and $P_2''/P_4''$ are 0 to 1, solutions for $P_4''$ and $\theta_4''$ can be converged by, for example, iteration and are therefore easily determined.

$P_4''$ and $\theta_4''$ are the fluorescence intensity and phase of fluorescence emitted by the acceptor-labeled sample directly excited by irradiation with laser light, which are calculated using a sample having a donor molecule and an acceptor molecule attached thereto. As can be seen also from the formula (21), fluorescence emitted by the acceptor molecule at the time when FRET occurs can be determined simply by adding the term representing FRET fluorescence to the term representing fluorescence emitted by the acceptor molecule by direct excitation. Therefore, the measurement results ($P_4''$ and $\theta_4''$) of the non-FRET sample cell (which has both an acceptor molecule and a donor molecule attached thereto) whose amount of label is equivalent to that of a FRET sample to be measured can be directly used as the fluorescence intensity and phase of fluorescence emitted by the acceptor-labeled sample directly excited by irradiation with laser light (i.e., $P_4''=P_4$ and $\theta_4''=\theta_4$).

As has been described above, the fluorescence relaxation time constant calculating unit 96 determines $\tau_d^*$ and $\tau_a^*$ by using the information calculated by the first calibration unit 88 to the fourth calibration unit 94 and stored in the memory 84 (e.g., the values of $P_2/P_4$, $P_3$ and $\theta_3$, $P_6$ and $\theta_6$, and $P_4$), the measured values $P_{donor}$ and $\theta_{donor}$ and $P_{acceptor}$ and $\theta_{acceptor}$ of the FRET sample 12, and the above formulas (20) and (21).

Then, the FRET efficiency calculating unit 98 determines FRET efficiency $E_t$ represented by the formula (22).

Figure 13:
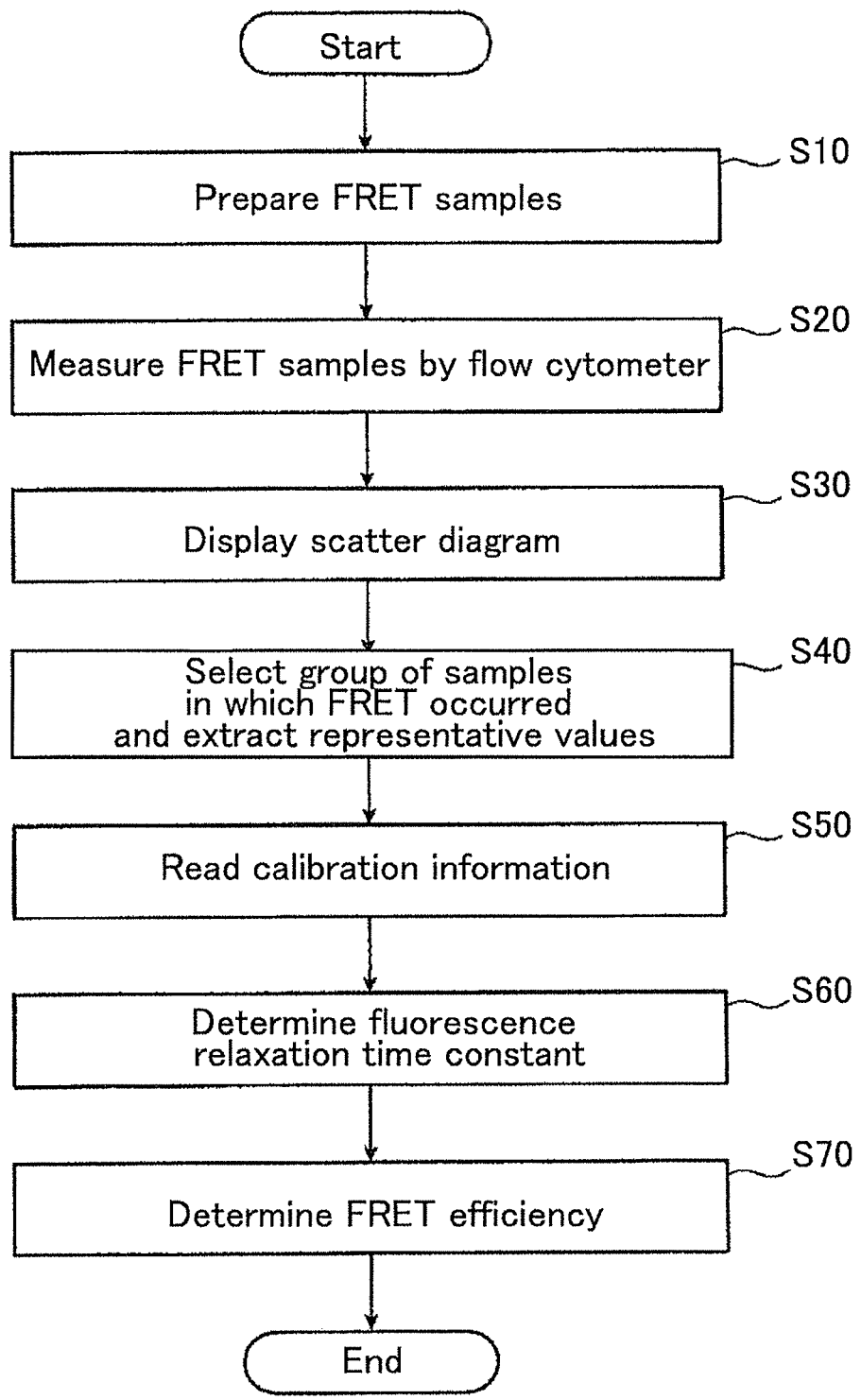
FIG. 13 is a flowchart of a FRET detection method carried out by the flow cytometer shown in FIG. 1.

Such a flow cytometer 10 as described above performs operations shown in FIG. 13 to determine FRET efficiency. The respective details of these operations are as described above. First, a FRET sample is prepared (Step S10). At this time, a plurality of FRET samples are suspended in a measurement solution. The FRET sample solution forms a flow cell in the tube line 30 with a sheath liquid. The flow cell is irradiated with laser light whose intensity is modulated at a predetermined frequency to measure fluorescence (Step S20).

The photoelectric converters 27a and 27b, which receive different wavelength bands of fluorescence, start fluorescence measurement in response to a trigger signal generated by the light-receiving unit 24 to indicate the timing of the passage of the FRET sample 12 through a measurement point in the tube line 30. A fluorescent signal obtained by the measurement is processed in the phase difference detector 56 in the signal processing unit 42 to extract a processing signal including the cos component of the fluorescence signal and a processing signal including the sin component of the fluorescence signal. These processing signals are supplied to the controller 44, a high-frequency signal is removed from each of the processing signals by the low-pass filter 62, and the cos component and the sin component of the fluorescence signal are determined by performing A/D conversion.

The thus determined cos component and sin component are supplied to the analysis device 80 to calculate measurement information (fluorescence intensity information and phase information on fluorescence within the donor wavelength band emitted by each of the FRET samples, fluorescence intensity information and phase information on fluorescence within the acceptor wavelength band of each of the FRET samples). Then, a scatter diagram (two-dimensional correlation diagram) is displayed on the display 94 (Step S30) by using the fluorescence intensity information on fluorescence within the donor wavelength band and the fluorescence intensity information on fluorescence within the acceptor wavelength band, each of information calculated within a predetermined measurement time.

Then, in order to specify the samples in which FRET occurred, a sample group of the fluorescence region of the samples in which FRET occurred is selected in the scatter diagram displayed on the display 94. The selection may be performed by using an input operation system such as a mouse by an operator or may be performed automatically by, for example, the CPU 82. The representative values of fluorescence intensity information and phase information on the FRET samples included in the region of the selected sample group (e.g., an average value, a gravity center value, and a frequency peak value) are determined (Step S40). The representative values are used as the above-mentioned $P_d$ and $\theta_d$ and $P_a$ and $\theta_a$.

Then, the individual pieces of calibration information (the first calibration information to the fourth calibration information) previously calculated by the first calibration unit 88 to the fourth calibration unit 94 and stored in the memory 84 are read from the memory 84 of the analysis device 80 (Step S50).

Then, $P_1$ and $\theta_1$ or $P_7$ and $\theta_7$ are calculated by using the above-mentioned $P_d$ and $\theta_d$ or $P_a$ and $\theta_a$ and the individual pieces of calibration information to determine $\tau_d^*$, $\tau_a^*$, or $\tau_a$, that is, the FRET fluorescence lifetime of donor molecule fluorescence component, the FRET fluorescence lifetime of acceptor molecule fluorescence component, or the non-FRET fluorescence lifetime of acceptor molecule fluorescence component. In the calculation, the fluorescence relaxation time constant unit 96 converts a formula such as the formula (20) or (21) represented by phases and amplitudes to a vector to sequentially perform vector operation (Step S60).

Then, for example, FRET efficiency $E_t$ is determined by using the fluorescence relaxation time constant $\tau_d$ of a fluorescence component within the donor wavelength band emitted by the donor molecule (which corresponds to the route $R_1$ in FIG. 5 in non-FRET state) (Step S70).

Figure 14:
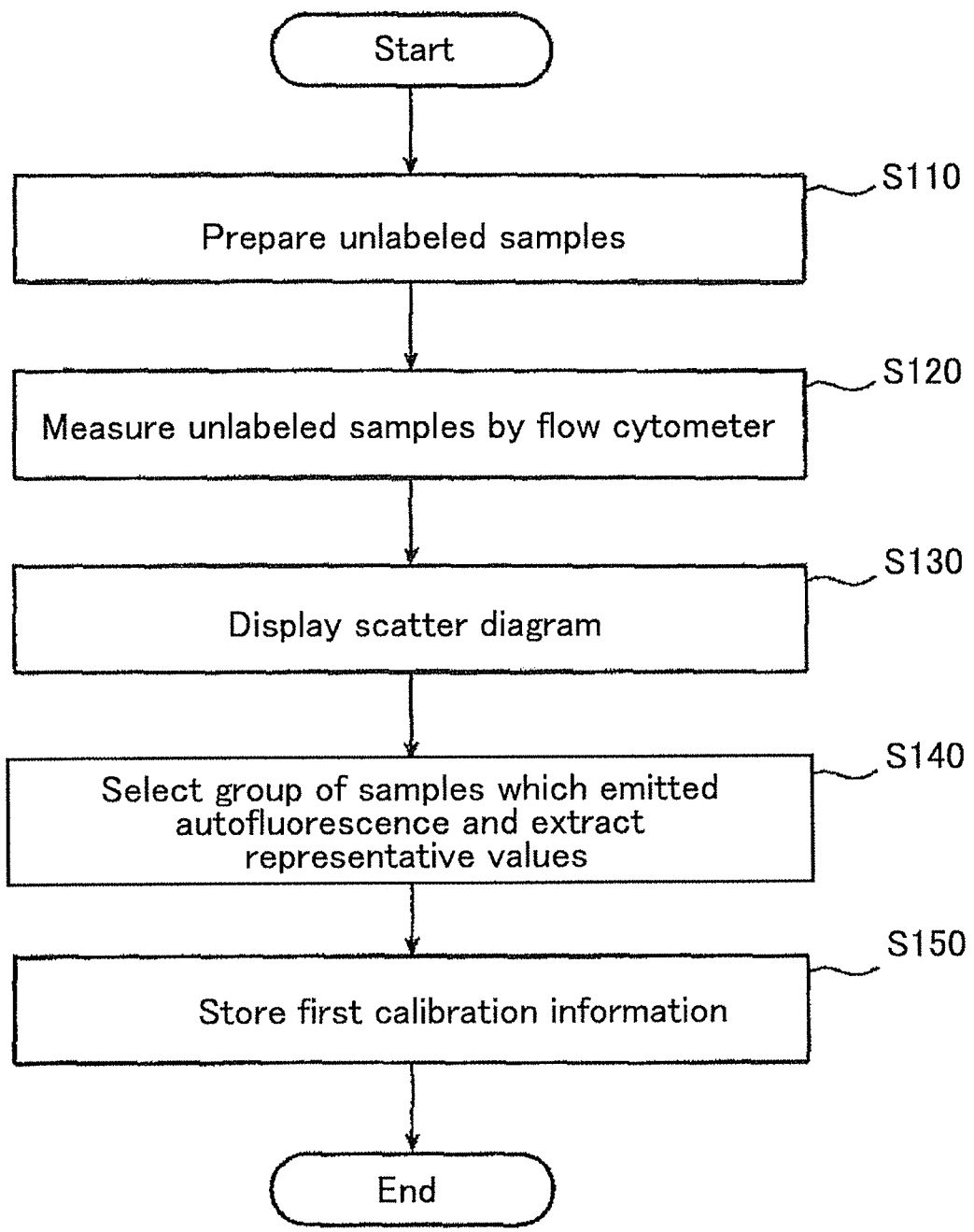
FIG. 14 is a flowchart of first calibration carried out by the flow cytometer shown in FIG. 1.

FIG. 14 is a flowchart of first calibration carried out by the flow cytometer 10. In the first calibration, unlabeled samples are first prepared (Step S110).

Then, the unlabeled samples are measured by the flow cytometer (Step S120). The measurement by the flow cytometer (Step S120), the display of a scatter diagram (Step S130), and the selection of a sample group of the fluorescence region of the unlabeled samples (Step S140) are the same operations as in Steps S20 to S40 shown in FIG. 13, and therefore descriptions thereof are omitted here. In the first calibration, representative values extracted in Step S140 are defined as the above-mentioned $P_{md1}$ and $\theta_{md1}$ and $P_{ma1}$ and $\theta_{ma1}$. The representative values $P_{md1}$ and $\theta_{md1}$ and $P_{ma1}$ and $\theta_{ma1}$ of measured information are stored as first calibration information in the memory 84 (Step S150). The first calibration information represents fluorescence intensity information $P_3$ and phase information $\theta_3$ on fluorescence within the donor wavelength band emitted by the cell itself when the unlabeled sample is irradiated with laser light and fluorescence intensity information $P_6$ and phase information $\theta_6$ on fluorescence within the acceptor wavelength band emitted by the cell itself when the unlabeled sample is irradiated with laser light. It is to be noted that the details of the individual pieces of information calculated by the first calibration (first calibration information) and of the operations performed in the first calibration are as described above.

Figure 15:
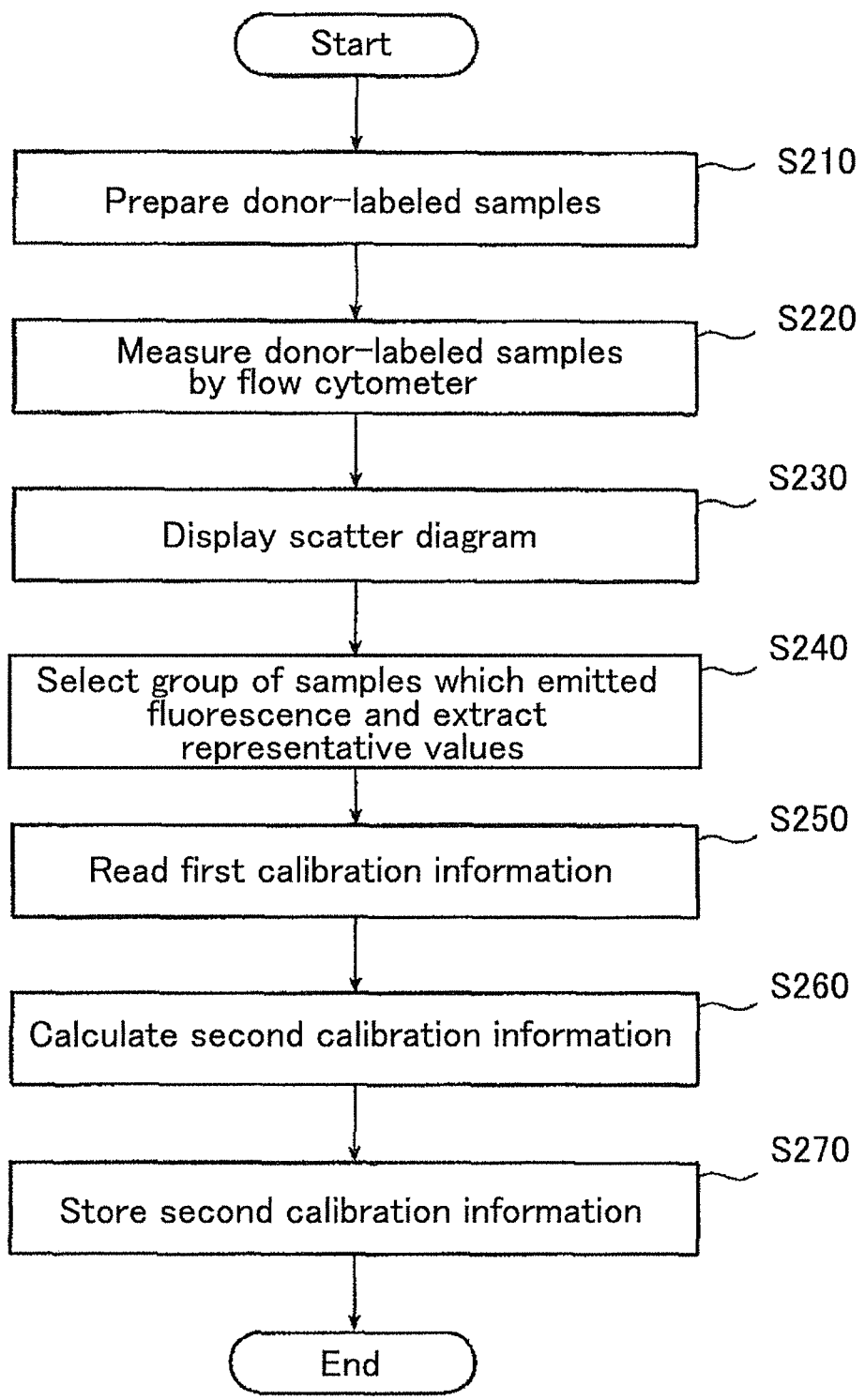
FIG. 15 is a flowchart of second calibration carried out by the flow cytometer shown in FIG. 1.

FIG. 15 is a flowchart of second calibration carried out by the flow cytometer 10. In the second calibration, donor-labeled samples are first prepared (Step S210).

Then, the donor-labeled samples are measured by the flow cytometer (Step S210). The measurement by the flow cytometer (Step S220), the display of a scatter diagram (Step S230), and the selection of a sample group of the fluorescence region of the donor-labeled samples (Step S240) are the same operations as in Steps S20 to S40 shown in FIG. 13, and therefore descriptions thereof are omitted here. In the second calibration, representative values extracted in Step S240 are defined as the above-mentioned $P_{md2}$ and $\theta_{md2}$ and $P_{ma2}$ and $\theta_{ma2}$. Then, the first calibration information calculated by the first calibration unit is read from the memory 84 (Step S250). Then, second calibration information is calculated by using $P_{md2}$ and $\theta_{md2}$ and $P_{ma2}$ and $\theta_{ma2}$ and the first calibration information (Step S260). The second calibration information includes $P_5/P_1$ representing the ratio of the fluorescence intensity of a fluorescence component within the acceptor fluorescence wavelength band emitted by the donor-labeled sample to the fluorescence intensity of a fluorescence component within the donor wavelength band emitted by the donor-labeled sample (i.e., leak rate of donor fluorescence). At this time, as described above, the fluorescence relaxation time constant $\tau_d$ of fluorescence within the donor wavelength band emitted by the donor molecule at the time when FRET does not occur and the fluorescence relaxation time constant $\tau_{da}$ of fluorescence within the acceptor wavelength band emitted by the donor molecule at the time when FRET does not occur are also determined. These constants are also included in the second calibration information. The second calibration information is stored in the memory 84 (Step S270). It is to be noted that the details of the second calibration information calculated by the second calibration and of the operations performed in the second calibration are as described above.

Figure 16:
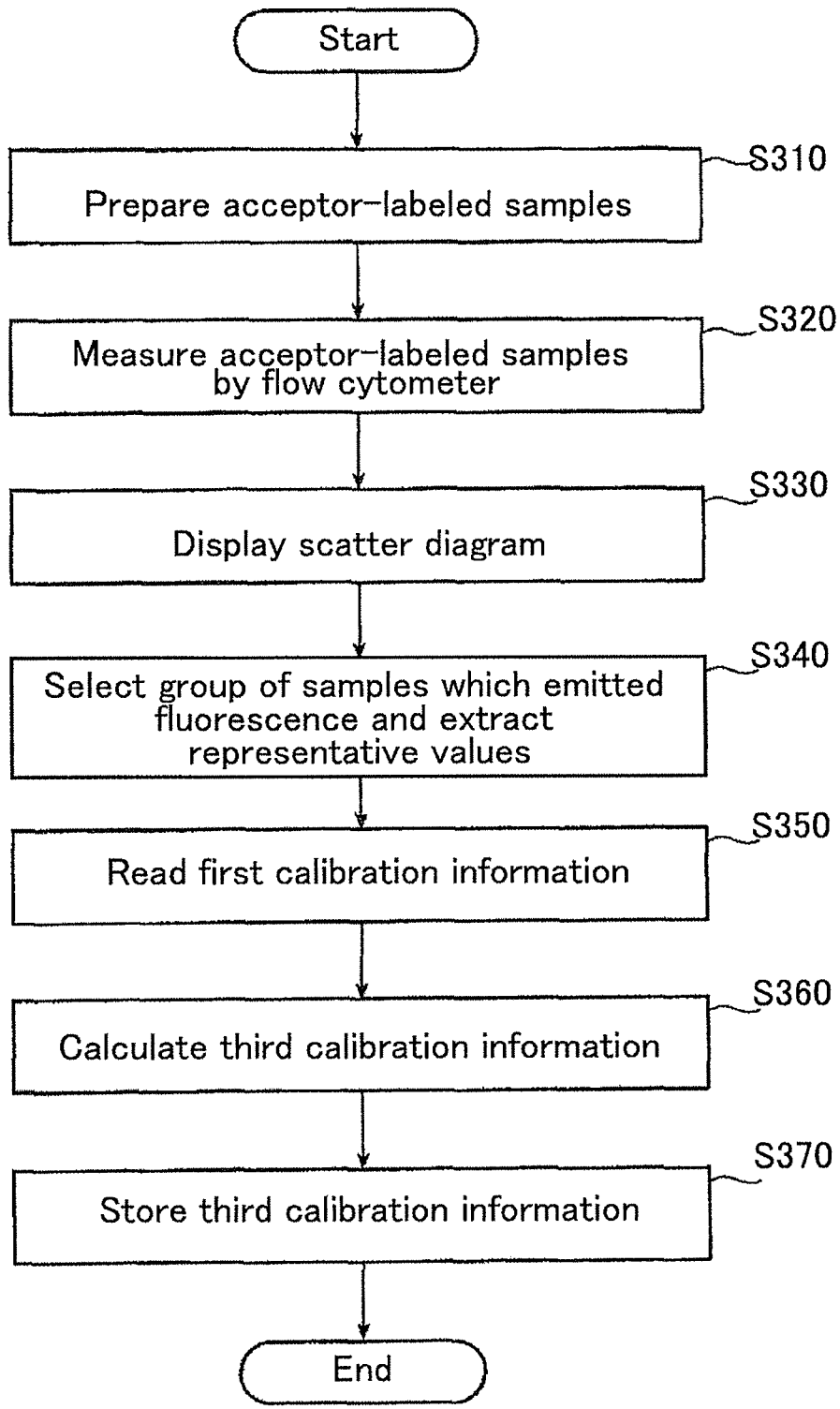
FIG. 16 is a flowchart of third calibration carried out by the flow cytometer shown in FIG. 1.

FIG. 16 is a flowchart of third calibration carried out by the flow cytometer 10. In the third calibration, acceptor-labeled samples are first prepared (Step S310).

Then, the acceptor-labeled samples are measured by the flow cytometer (Step S320). The measurement by the flow cytometer (Step S320), the display of a scatter diagram (Step S330), and the selection of a sample group of the fluorescence region of the acceptor-labeled samples (Step S340) are the same operations as in Steps S20 to S40 shown in FIG. 13, and therefore descriptions thereof are omitted here. In the third calibration, representative values extracted in Step S340 are defined as the above-mentioned $P_{md3}$ and $\theta_{md3}$ and $P_{ma3}$ and $\theta_{ma3}$. Then, the first calibration information calculated by the first calibration unit is read from the memory 84 (Step S350). Then, third calibration information is calculated by using the $P_{md3}$ and $\theta_{md3}$ and $P_{ma3}$ and $\theta_{ma3}$ and the first calibration information (Step S360). The second calibration information includes $P_2/P_4$ representing the ratio of the fluorescence intensity of a fluorescence component within the donor fluorescence wavelength band emitted by the acceptor-labeled sample to the fluorescence intensity of a fluorescence component within the acceptor wavelength band emitted by the acceptor-labeled sample (i.e., leak rate of acceptor fluorescence). At this time, as described above, the fluorescence relaxation time constant $\tau_a$ of fluorescence within the acceptor wavelength band emitted by the acceptor molecule at the time when FRET does not occur and the fluorescence relaxation time constant $\tau_{ad}$ of fluorescence within the donor wavelength band emitted by the acceptor molecule at the time when FRET does not occur are also determined. These constants are also included in the third calibration information. The third calibration information is stored in the memory 84 (Step S370). It is to be noted that the details of the third calibration information calculated by the third calibration and of the operations performed in the third calibration are as described above.

Figure 17:
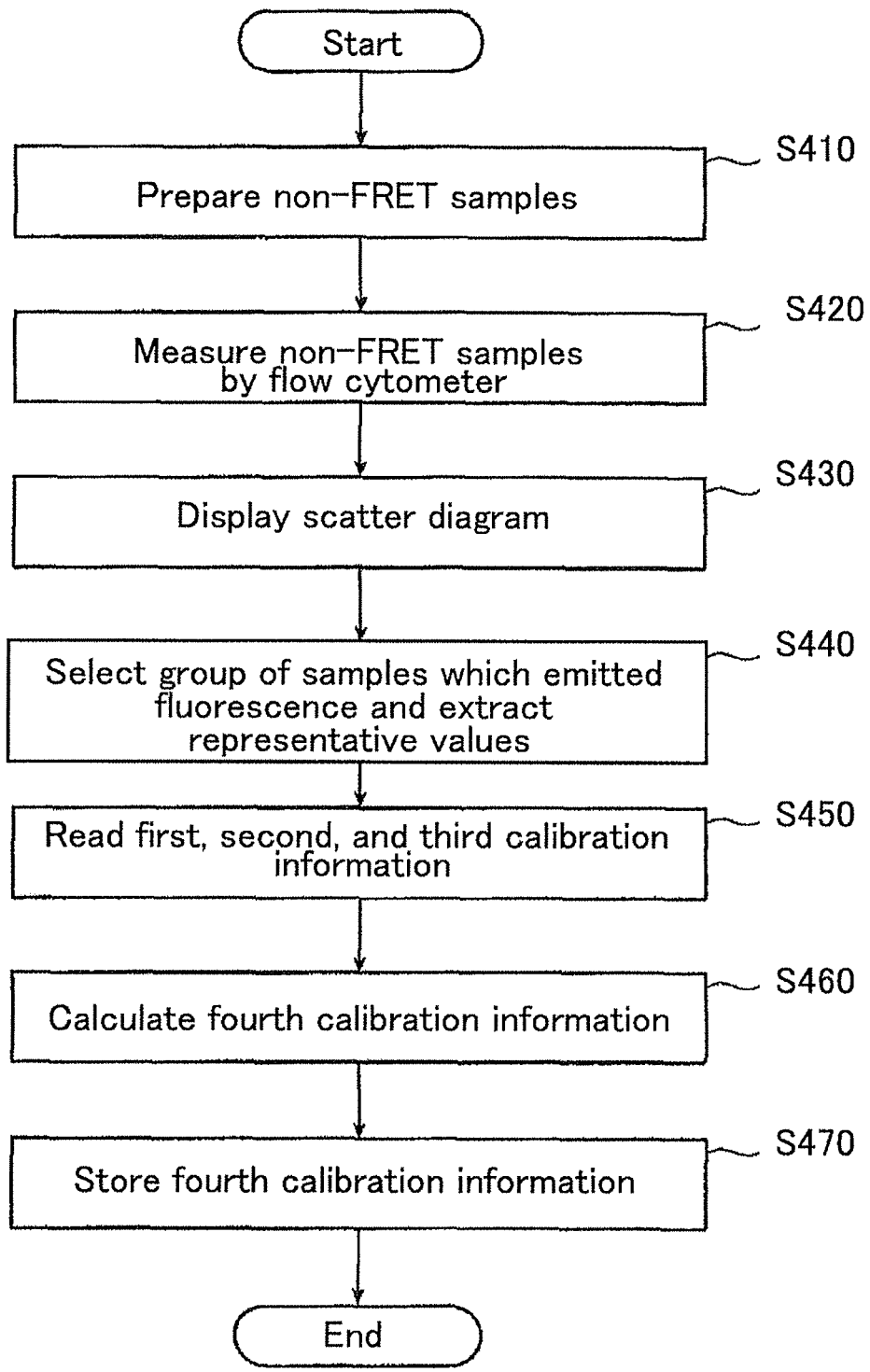
FIG. 17 is a flowchart of fourth calibration carried out by the flow cytometer shown in FIG. 1.

FIG. 17 is a flowchart of fourth calibration carried out by the flow cytometer 10. In the fourth calibration, non-FRET samples are first prepared (Step S410).

Then, the non-FRET samples are measured by the flow cytometer (Step S420). The measurement by the flow cytometer (Step. S420), the display of a scatter diagram (Step S430), and the selection of a sample group of the fluorescence region of the non-FRET samples (Step S440) are the same operations as in Steps S20 to S40 shown in FIG. 13, and therefore descriptions thereof are omitted here. In the fourth calibration, representative values extracted in Step S440 are defined as the above-mentioned $P_{md4}$ and $\theta_{md4}$ and $P_{ma4}$ and $\theta_{ma4}$. Then, the first to third calibration information calculated by the first to third calibration units is read from the memory 84 (Step S450). Then, fourth calibration information is calculated by using $P_{md4}$ and $\theta_{md4}$ and $P_{ma4}$ and $\theta_{ma4}$ and the first to third calibration information (Step S460). The fourth calibration information includes information on the fluorescence intensity $P_4$ and phase $\theta_4$ of fluorescence emitted by the acceptor-labeled sample directly excited by irradiation with laser light. The thus calculated fourth calibration information is stored, in the memory 84 (Step S470). The individual pieces of calibration information calculated by the first to fourth calibrations are used for FRET detection performed using FRET samples according to the flowchart shown in FIG. 13. It is to be noted that the details of the individual pieces of information determined by the fourth calibration (fourth calibration information) and of the operations performed in the fourth calibration are as described above.

As described above, in the present invention, the leak rate of donor molecule fluorescence ($P_5/P_1$) and the leak rate of acceptor fluorescence ($P_2/P_4$), which do not change depending on the amount of label attached to a target of FRET measurement, are previously calculated using samples (e.g., donor-labeled samples and acceptor-labeled samples) different from the FRET samples in the amount of label attached. By processing measured information on the FRET samples using such previously-calculated information such as the leak rates, it is possible to determine the fluorescence lifetime of the FRET sample with a high degree of accuracy. Further, fluorescence components emitted by the acceptor molecule directly excited by irradiation with laser light are previously determined using non-FRET samples treated so as not to cause FRET. By processing measured information on the FRET samples using such previously-calculated information, it is possible to determine the fluorescence lifetime of the FRET sample with a high degree of accuracy. Further, by removing autofluorescence components emitted by the cell itself having the donor molecule and the acceptor molecule attached thereto, it is possible to determine the fluorescence lifetime of the FRET sample with a higher degree of accuracy.

It is to be noted that the above embodiment uses non-FRET samples, each of which has both the donor fluorescent molecule and the acceptor fluorescent molecule and has been treated so as not to cause FRET by introducing a factor which inactivates protein structural change or protein linkage. By calculating information on the fluorescence intensity and phase of fluorescence emitted by the non-FRET sample, the fluorescence intensity and phase of fluorescence components emitted by the acceptor-labeled sample directly excited by irradiation with laser light are determined. For example, in a case where a sample labeled with the acceptor molecule is irradiated with two laser beams with different wavelengths so that fluorescence is emitted by the acceptor molecule excited by irradiation with the laser beams, it can be assumed that the ratio between fluorescence components within one wavelength band emitted by irradiation with the two laser beams is constant irrespective of the amount of label attached to a sample to be measured. More specifically, it can be assumed that when the ratio between fluorescence components emitted by the FRET sample by irradiation with the two laser beams is changed relative to the ratio between fluorescence components emitted by the acceptor-labeled sample by irradiation with the two laser beams, the amount of change is due to FRET. It can be said, when the ratio between fluorescence components emitted by the acceptor-labeled sample by irradiation with the two laser beams is previously calculated, fluorescence intensity information and phase information on fluorescence components emitted by the acceptor-labeled sample directly excited by laser can be determined by calculating the ratio between fluorescence components emitted by the FRET sample by irradiation with the two laser beams. In the present invention, fluorescence intensity information and phase information on fluorescence components emitted by the acceptor-labeled sample directly excited by laser may be calculated by such a method. It is to be noted that as a means for detecting fluorescence components emitted by irradiation with two laser beams independently, a means described in Japanese Patent Application Nos. 2005-37399 and 2006-054347, which are previous patent applications by the present inventors, can be used.

The FRET detection method and FRET detection device according to the present invention have been described in detail, but the present invention is not limited to the above-described embodiments and, various changes and modifications can be made without departing from the scope and sprit of the present invention.

What is claimed is:

1. A FRET detection method of detecting FRET (Fluorescence Resonance Energy Transfer) in which energy of a donor molecule is transferred to an acceptor molecule, the method comprising the steps of:
   a) measuring fluorescence emitted from each of samples by two or more detection sensors having different light-receiving wavelength bands, each of the samples being labeled with a donor molecule and an acceptor molecule and being irradiated with laser light whose intensity is modulated at a predetermined frequency, to acquire detection values including fluorescence intensity information and phase information on the fluorescence emitted from each of the samples;
   b) reading calibration information previously stored in a memory means, which includes at least a first intensity ratio that is a ratio between fluorescence intensities at the light-receiving wavelength bands of a donor molecule fluorescence component emitted from the donor molecule included in the fluorescence emitted from each of the samples, phase information on the donor molecule fluorescence component relative to the modulated laser light, a second intensity ratio that is a ratio between fluorescence intensities at the light-receiving wavelength bands of an acceptor molecule fluorescence component emitted from the acceptor molecule included in the fluorescence, phase information on the acceptor molecule fluorescence component relative to the laser light, and a non-FRET fluorescence lifetime of the donor molecule fluorescence component when the FRET does not occur, which is a lifetime defined by assuming that fluorescence emitted from the donor molecule excited by laser light is a relaxation response of a first-order lag system;
   c) calculating fluorescence intensity information and phase information on the fluorescence at each of the light-receiving wavelength bands, based on the detection values, and determining a FRET fluorescence lifetime of the donor molecule fluorescence component, which is defined by assuming that fluorescence emitted from the donor molecule excited by laser light is a relaxation response of a first-order lag system, using the calculated fluorescence intensity information, the calculated phase information, the first intensity ratio, the phase information on the donor molecule fluorescence component, the second intensity ratio, the phase information on the acceptor molecule fluorescence component; and
   d) determining information on FRET occurrence using a ratio between the FRET fluorescence lifetime of the donor molecule fluorescence component and the non-FRET fluorescence lifetime of the donor molecule fluorescence component.

2. The FRET detection method according to claim 1, wherein in the step d), FRET efficiency $E_t$ is determined as the information on the occurrence of FRET, which is represented by $1-(\tau_d^*/\tau_d)$, wherein $\tau_d$ is the non-FRET fluorescence lifetime of the donor molecule fluorescence component and $\tau_d^*$ is the FRET fluorescence lifetime of the donor molecule fluorescence component.

3. The FRET detection method according to claim 1, wherein
   in the step c), fluorescence intensity information and phase information on each of the samples are calculated based on each of the detection values and the FRET fluorescence lifetime is determined based on the calculated multiple pieces of fluorescence intensity information and phase information.

4. The FRET detection method according to claim 1, wherein in the step c), the fluorescence intensity information and the phase information calculated at each of the light-receiving wavelength bands are represented as a vector, and fluorescence intensity information and phase information on the donor molecule fluorescence component and fluorescence intensity information and phase information on a FRET component of an acceptor molecule fluorescence component which is emitted by the acceptor molecule on the occurrence of FRET are calculated at, and the FRET fluorescence lifetime is determined by using the calculated information.

5. The FRET detection method according to claim 4, further comprising the steps of:

preparing a predetermined sample which is each of the samples unlabeled with the donor molecule and the acceptor molecule and emits autofluorescence when irradiated with the laser light;

measuring, at each of the light-receiving wavelength bands, the autofluorescence emitted by the predetermined sample which is irradiated with the laser light;

calculating fluorescence intensity information and phase information on the autofluorescence from the measured autofluorescence within each of the light-receiving wavelength bands to store the calculated fluorescence intensity information and phase information in the memory means;

wherein in the step b), the stored fluorescence intensity information and the phase information on the autofluorescence are read from the memory means and the read fluorescence intensity information and the phase information on the autofluorescence are represented as a vector, and in the step c), the vector of the autofluorescence is subtracted from each vector at the light-receiving wavelength bands of the samples to be measured, and the FRET fluorescence lifetime is determined using a vector obtained by the subtraction.

6. The FRET detection method according to claim 5, wherein the autofluorescence is measured by each of the detection sensors by irradiating the predetermined sample as a measuring object with laser light whose intensity is modulated at a predetermined frequency.

7. The FRET detection method according to claim 4, wherein the light-receiving wavelength bands include a first wavelength band centered around a peak wavelength at which a fluorescence intensity of the donor molecule fluorescence component is maximum and a second wavelength band centered around a peak wavelength at which a fluorescence intensity of the acceptor molecule fluorescence component is maximum, in the step c), fluorescence intensity information and phase information on the donor molecule fluorescence component emitted are calculated using at least the second intensity ratio and the vector at the first wavelength band represented by the detection values acquired from the detection sensors with the first wavelength band, and fluorescence intensity information and phase information on the FRET component are calculated using at least the first intensity ratio and the vector at the second wavelength band represented by the detection values acquired from the detection sensors with the second wavelength band.

8. The FRET detection method according to claim 7, wherein the memory means previously stores fluorescence intensity information and phase information on a directly-excited fluorescence component of the acceptor molecule fluorescence component, the directly-excited fluorescence component being emitted by the acceptor molecule directly excited by the laser light, in the step b), fluorescence intensity information and phase information on the directly-excited fluorescence component are read from the memory means to represent the information on the directly-excited fluorescence component as a vector, and in the step c), fluorescence intensity information and phase information on the acceptor molecule fluorescence component emitted at the time when the FRET occurs are calculated using at least the vector of the directly-excited fluorescence component and the vector at the second wavelength band.

9. The FRET detection method according to claim 7, wherein the memory means previously stores fluorescence intensity information and phase information on a directly-excited fluorescence component of the acceptor molecule fluorescence component, the directly-excited fluorescence component being emitted by the acceptor molecule directly excited by the laser light, in the step b), fluorescence intensity information and phase information on the directly-excited fluorescence component are read from the memory means and then represented as a vector of the directly-excited fluorescence component, and in the step c), phase information on the FRET component is further calculated using at least the vector at the second wavelength band and the first intensity ratio, and a FRET fluorescence lifetime of the acceptor molecule fluorescence component emitted at the time when the FRET occurs and a non-FRET fluorescence lifetime of the acceptor molecule fluorescence component emitted at the time when the FRET does not occur are determined using the calculated phase information on the FRET component and the vector of the directly-excited fluorescence component, and a FRET fluorescence lifetime of the donor molecule fluorescence component is determined using the FRET fluorescence lifetime of the acceptor molecule fluorescence component and the non-FRET fluorescence lifetime of the acceptor molecule fluorescence component.

10. The FRET detection method according to claim 1, further comprising the steps of:

preparing a non-FRET sample which is labeled with the donor molecule and the acceptor molecule and which has been treated not to cause FRET;

measuring, at each of the light-receiving wavelength bands, fluorescence emitted by the non-FRET sample which is irradiated with the laser light; and calculating fluorescence intensity information and phase information on the a directly-excited fluorescence component emitted by the acceptor molecule directly excited by laser light within each of the light-receiving wavelength bands from the measured fluorescence, using the first intensity ratio previously stored in the memory means, the phase information on the donor molecule fluorescence component, the second intensity ratio previously stored in the memory means, and the phase information on the acceptor molecule fluorescence component, to store the calculated fluorescence intensity information and phase information in the memory means.

11. The FRET detection method according to claim 10,
wherein the non-FRET sample is a sample obtained by labeling, with the donor molecule and the acceptor molecule, a predetermined sample which emits autofluorescence when excited by the laser light,
the method further comprising the steps of:
preparing the predetermined sample;
measuring, at each of the light-receiving wavelength bands, the autofluorescence emitted by the predetermined sample which is irradiated with the laser light;
calculating fluorescence intensity information and phase information on the autofluorescence from the measured autofluorescence within each of the light-receiving wavelength bands, to store the calculated fluorescence intensity information and phase information on the autofluorescence in the memory means;
subtracting an autofluorescence vector representing the fluorescence intensity information and phase information on the autofluorescence from a non-FRET sample vector representing fluorescence intensity information and phase information on fluorescence emitted by the non-FRET sample; and
calculating a directly-excited fluorescence component vector representing the fluorescence intensity information and phase information on the directly-excited fluorescence component, using a vector obtained by the subtraction.

12. The FRET detection method according to claim 1,
the method further comprising the steps of:
preparing a donor molecule sample which is labeled with only the donor molecule;
measuring, at each of the light-receiving wavelength bands, fluorescence emitted by the donor molecule of the donor molecule sample which is irradiated with the laser light;
calculating fluorescence intensity information and phase information on the measured fluorescence emitted by the donor molecule sample within each of the light-receiving wavelength bands, to obtain the first intensity ratio; and
storing the phase information on the measured fluorescence and the first intensity ratio.

13. The FRET detection method according to claim 12,
wherein the donor molecule sample is a sample obtained by labeling, with the donor molecule, a predetermined sample which emits autofluorescence when excited by the laser light,
the method further comprising the steps of:
preparing the predetermined sample;
measuring, at each of the light-receiving wavelength bands, the autofluorescence emitted by the predetermined sample which is irradiated with the laser light;
calculating fluorescence intensity information and phase information on the autofluorescence from the measured autofluorescence within each of the light-receiving wavelength bands to store the calculated fluorescence intensity information and phase information in the memory means;
subtracting an autofluorescence vector representing the fluorescence intensity information and phase information on the autofluorescence from a donor molecule sample vector representing fluorescence intensity information and phase information on fluorescence emitted by the donor molecule sample; and
calculating the fluorescence intensity information and phase information on the fluorescence emitted by the donor molecule sample, using a vector obtained by the subtraction.

14. The FRET detection method according to claim 1,
the method further comprising the steps of:
preparing an acceptor molecule sample which is labeled with only the acceptor molecule;
measuring, at each of the light-receiving wavelength bands, fluorescence emitted by the acceptor molecule of the acceptor molecule sample which is irradiated with the laser light;
calculating fluorescence intensity information and phase information on the measured fluorescence emitted by the acceptor molecule sample within each of the light-receiving wavelength bands, to obtain the second intensity ratio; and
storing the phase information on the measured fluorescence and the second intensity ratio.

15. The FRET detection method according to claim 14,
wherein the acceptor molecule sample is a sample obtained by labeling, with the acceptor molecule, a predetermined sample which emits autofluorescence when excited by the laser light,
the method further comprising the steps of:
preparing the predetermined sample;
measuring, at each of the light-receiving wavelength bands, the autofluorescence emitted by the predetermined sample which is irradiated with the laser light;
calculating fluorescence intensity information and phase information on the autofluorescence from the measured autofluorescence within each of the light-receiving wavelength bands, to store the calculated fluorescence intensity information and phase information in the memory means;
subtracting an autofluorescence vector representing the fluorescence intensity information and phase information on the autofluorescence from an acceptor molecule sample vector representing fluorescence intensity information and phase information on fluorescence emitted by the acceptor molecule sample; and
calculating the fluorescence intensity information and phase information on the fluorescence emitted by the acceptor molecule sample, using a vector obtained by the subtraction.

16. A device for detecting FRET (Fluorescence Resonance Energy Transfer), in which energy of a donor molecule transfers to an acceptor molecule, the device comprising:
an information acquiring unit which acquires detection values, each values including fluorescence intensity information and phase information on fluorescence emitted by each of the samples to be measured by allowing two or more detection sensors different in light-receiving wavelength band to receive fluorescence emitted by each of the samples to be measured, each of the samples being labeled with a donor molecule and an acceptor molecule and being irradiated with laser light whose intensity is modulated at a predetermined frequency;
a memory means for previously storing calibration information including at least a first intensity ratio that is a ratio between fluorescence intensities at the light-receiving wavelength bands of a donor molecule fluorescence component emitted by the donor molecule included in the fluorescence emitted by each of the samples to be measured, phase information on the donor molecule fluorescence component, an acceptor intensity ratio that is a ratio between fluorescence intensities at the light-receiving wavelength bands of an acceptor molecule fluorescence component emitted by the acceptor molecule, phase information of the acceptor molecule fluorescence component, and a non-FRET fluorescence lifetime of the donor molecule fluorescence component emitted at the time when the FRET does not occur, which is a lifetime defined by assuming that fluorescence emitted by the donor molecule excited by laser light is a relaxation response of a first-order lag system;

a FRET fluorescence lifetime calculating unit which calculates fluorescence intensity information and phase information on fluorescence within each of the light-receiving wavelength bands emitted by each of the samples to be measured based on the detection values acquired by the information acquiring unit, and determines a FRET fluorescence lifetime of the donor molecule fluorescence component, which is defined by assuming that fluorescence emitted by the donor molecule excited by laser light is a relaxation response of a first-order lag system, by using the calculated fluorescence intensity information, the calculated phase information, the first intensity ratio read from the memory means, the phase information on the donor molecule fluorescence component, the second intensity ratio, and the phase information on the acceptor molecule fluorescence component; and a FRET occurrence information calculating unit which determines information on the occurrence of FRET represented by a ratio between the FRET fluorescence lifetime of the donor molecule fluorescence component and the non-FRET fluorescence lifetime of the donor molecule fluorescence component.

17. The FRET detection device according to claim 16, wherein in the FRET fluorescence lifetime calculating unit, the fluorescence intensity information and the phase information calculated from each of the detection values are represented as a vector, and fluorescence intensity information and phase information on the donor molecule fluorescence component and fluorescence intensity information and phase information on a FRET component of an acceptor molecule fluorescence component which is emitted by the acceptor molecule at the time when the FRET occurs, are calculated using the vector, the first intensity ratio, the phase information on the donor molecule fluorescence component, the second intensity ratio of the acceptor molecule fluorescence component, and the phase information on the acceptor molecule fluorescence component, and the FRET fluorescence lifetime is determined by using the calculated information.

18. The FRET detection device according to claim 16, wherein the respective light-receiving wavelength bands of the sensors are a first wavelength band centered around a peak wavelength at which a fluorescence intensity of the donor molecule fluorescence component is maximum and a second wavelength band centered around a peak wavelength at which a fluorescence intensity of the acceptor molecule fluorescence component is maximum, and the FRET fluorescence lifetime calculating unit calculates fluorescence intensity information and phase information on the donor molecule fluorescence component by using at least a vector at the first wavelength band determined from the detection value acquired from one of the detection sensors with the first wavelength band and the second intensity ratio, and calculates fluorescence intensity information and phase information on the FRET component by using at least a vector at the second wavelength band represented by the detection value acquired from one of the detection sensors with the second wavelength band and the first intensity ratio.

19. The FRET detection device according to claim 16, further comprising an autofluorescence calibration unit, wherein the autofluorescence calibration unit acquires a detection value including fluorescence intensity information and phase information at each of the light-receiving wavelength bands from each of the detection sensors by irradiating, with the laser, light a predetermined sample which is each of the samples unlabeled with the donor molecule and the acceptor molecule and emits autofluorescence when irradiated with the laser light, calculates fluorescence intensity information and phase information on the autofluorescence within each of the light-receiving wavelength bands, and stores the calculated fluorescence intensity information and the calculated phase information on the autofluorescence in the memory means, and in the FRET fluorescence lifetime calculating unit, a vector representing the fluorescence intensity information and the phase information on the autofluorescence is subtracted from a vector representing information on fluorescence within each of the light-receiving wavelength bands emitted by the sample to be measured, and the FRET fluorescence lifetime is determined using a vector obtained by the subtraction.

20. The FRET detection device according to claim 16, further comprising a non-FRET calibration unit, wherein the non-FRET calibration unit calculates fluorescence intensity information and phase information on fluorescence within each of the light-receiving wavelength bands emitted by a non-FRET sample, which has the donor and acceptor molecules attached thereto and which has been treated so as not to cause FRET, when a detection value including fluorescence intensity information and phase information at each of the light-receiving wavelength bands is acquired from each of the detection sensors by irradiating the non-FRET sample with the laser light, and calculates fluorescence intensity information and phase information on a directly-excited fluorescence component emitted by the acceptor molecule directly excited by the laser light by using the calculated fluorescence intensity information, the calculated phase information, the first intensity ratio, the phase information on the donor molecule fluorescence component, the second intensity ratio, and the phase information on the acceptor molecule fluorescence component, and derives a directly-excited fluorescence component vector representing the calculated information, and stores a derived result in the memory means, and the FRET fluorescence lifetime calculating unit determines the FRET fluorescence lifetime by using the directly-excited fluorescence component vector.

21. The FRET detection device according to claim 16, further comprising a donor molecule calibration unit, wherein the donor molecule calibration unit calculates fluorescence intensity information and phase information on fluorescence within each of the light-receiving wavelength bands emitted by a donor molecule sample, which is each of the samples labeled with only the donor molecule, when the donor molecule sample irradiated with the laser light emits fluorescence and a detection value including fluorescence intensity information and phase information on the fluorescence within each of the light-receiving wavelength bands emitted by the donor molecule sample is acquired from each of the detection sensors, and calculates the first intensity ratio, and stores the calculated first intensity ratio and the calculated phase information on fluorescence emitted by the donor molecule sample in the memory means.

22. The FRET detection device according to claim 16, further comprising a second molecule calibration unit,
wherein the second molecule calibration unit calculates fluorescence intensity information and phase information on fluorescence within each of the light-receiving wavelength bands emitted by an acceptor molecule sample, which is each of the samples labeled with only the acceptor molecule, when the acceptor molecule sample irradiated with the laser light emits fluorescence and a detection value including fluorescence intensity information and phase information on the fluorescence within each of the light-receiving wavelength bands emitted by the acceptor molecule sample is acquired from each of the detection sensors, and calculates, the second intensity ratio, and stores the calculated second intensity ratio and the calculated phase information on fluorescence emitted by the acceptor molecule sample in the memory means.

* * * * *